(12) United States Patent
Chang et al.

(10) Patent No.: US 10,151,585 B1
(45) Date of Patent: Dec. 11, 2018

(54) NON-CONTACT AND OPTICAL MEASURING AUTOMATION SYSTEM FOR THE SURFACE ROUGHNESS VALUE OF DISK CAMS AND METHOD THEREOF

(71) Applicant: National Taiwan Ocean University, Keelung (TW)

(72) Inventors: Wen-Tung Chang, Taipei (TW); Chun-Cheng Lu, New Taipei (TW); Hsiang-Lun Kao, New Taipei (TW)

(73) Assignee: National Taiwan Ocean University, Keelung (TW)

(*) Notice: Subject to any disclaimer, the term of this patent is extended or adjusted under 35 U.S.C. 154(b) by 0 days.

(21) Appl. No.: 15/824,678

(22) Filed: Nov. 28, 2017

(30) Foreign Application Priority Data

Aug. 25, 2017 (TW) .............................. 106129072 A

(51) Int. Cl.
| | |
|---|---|
| *G01B 11/30* | (2006.01) |
| *G01N 21/00* | (2006.01) |
| *G01N 21/89* | (2006.01) |
| *F16H 53/00* | (2006.01) |
| *G01N 21/47* | (2006.01) |

(52) U.S. Cl.
CPC .............. *G01B 11/30* (2013.01); *F16H 53/00* (2013.01); *G01N 21/4788* (2013.01); *G01N 21/8901* (2013.01); *G01N 2021/479* (2013.01)

(58) Field of Classification Search
CPC ............ G01B 11/2425; G01B 11/2433; G01B 11/08; G01B 11/2408; G01B 11/02; G01B 11/06; G01B 11/30; G06T 7/0004; G06T 7/0085; G06T 7/0089; B23B 3/24; B23B 2251/426; G01N 21/8901; G01N 21/4788; G01N 2021/479; F16H 53/00
See application file for complete search history.

(56) References Cited

U.S. PATENT DOCUMENTS

| | | | |
|---|---|---|---|
| 5,329,458 A * | 7/1994 | Unno ................... | G01B 11/028 700/195 |
| 7,538,879 B2 * | 5/2009 | Power ................ | G01N 21/8422 356/432 |
| 8,755,055 B2 * | 6/2014 | Khajornrungruang ...................... | B23Q 17/2233 29/407.1 |
| 2007/0229853 A1 * | 10/2007 | Cheng ................ | B23Q 17/2233 356/625 |

(Continued)

*Primary Examiner* — Sang H Nguyen
(74) *Attorney, Agent, or Firm* — Huffman Law Group, PC

(57) ABSTRACT

A non-contact and optical measuring automation system includes a base, a rotating chuck to clamp a disk cam, a moving stage module and an optical measuring module. The moving stage module includes a first linear motion stage movably disposed on the base, a second linear motion stage movably disposed on the first linear motion stage, and a rotary motion stage rotatably disposed on the second linear motion stage. The optical measuring module disposed on the rotary motion stage includes a laser-emitting unit and an image-capturing unit. The laser-emitting unit projects a light beam onto a cam surface of the disk cam, and the image-capturing unit receives scattering light to capture a grayscale measuring image including a profile speckle pattern. A computer calculates a profile speckle characteristic value according to the grayscale measuring image and the surface roughness value according to the profile speckle characteristic value.

4 Claims, 22 Drawing Sheets

(56) References Cited

U.S. PATENT DOCUMENTS

| | | | | |
|---|---|---|---|---|
| 2008/0123106 | A1* | 5/2008 | Zeng | A61B 5/0066 356/600 |
| 2011/0128552 | A1* | 6/2011 | Hadcock | G01B 5/0004 356/496 |
| 2012/0236139 | A1* | 9/2012 | Chang | G01B 11/02 348/88 |
| 2014/0148658 | A1* | 5/2014 | Zalevsky | A61B 5/14532 600/301 |
| 2015/0017879 | A1* | 1/2015 | Chang | B24B 19/00 451/5 |
| 2016/0187121 | A1* | 6/2016 | Chang | G01B 11/2425 356/630 |

\* cited by examiner

NON-CONTACT AND OPTICAL MEASURING AUTOMATION SYSTEM FOR THE SURFACE ROUGHNESS VALUE OF DISK CAMS AND METHOD THEREOF

CROSS-REFERENCE TO RELATED APPLICATIONS

This non-provisional application claims priority under 35 U.S.C. § 119(a) on Patent Application No(s). 106129072 filed in Taiwan R.O.C. on Aug. 25, 2017, the entire contents of which are hereby incorporated by reference.

TECHNICAL FIELD

The present disclosure provides a measuring automation system and a method for measuring the surface roughness value of a disk cam, more particular to a non-contact and optical measuring automation system and a non-contact and optical method for measuring the surface roughness value of the disk cam.

BACKGROUND

Cams are mechanical components widely used in various machines and automation equipment. The cam makes its follower to produce a prescribed motion through direct contact in order to achieve required motion control. Generally, the profile of a disk cam is machined by using a computer numerical control (CNC) machine, and the profile surface of the disk cam is then ground in order to achieve good surface roughness. An excessive surface roughness value of the cam profile will increase the degree of wear between the disk cam and the follower in contact with each other. Such a situation will also influence the dynamic performance of the cam mechanism so as to produce excessive vibration and noise in high-speed operations. Therefore, after the manufacturing processes for the disk cam, the surface roughness value of the disk cam must be inspected for quality control.

The surface roughness value of the disk cam could to be measured by using a conventional contact type measuring equipment. A stylus of the contact type measuring equipment contacts a part of the cam surface to measure the surface roughness value at this part. However, the measured part of the cam surface cannot have too large curvature change; otherwise, this measured part will exceed a measurable range of the stylus. In other words, a traverse length of the contact type measuring equipment should be set to a quite small value so as to ensure that the measured part of the cam surface where the stylus contacts has extremely small curvature change, which causes a low measuring efficiency of the contact type measuring equipment. Further, since the stylus of the contact type measuring equipment contacts the cam frequently during the measurement, gradual wear of the stylus will unavoidably occur.

SUMMARY

According to one aspect of the present disclosure, a non-contact and optical measuring automation system, configured for electrically connected to a computer to measure a surface roughness value of a cam surface of a disk cam, includes a base, a rotating chuck, a moving stage module and an optical measuring module. The rotating chuck is disposed on the base to clamp the disk cam, thereby allowing the disk cam to be rotatable around a rotational axis of the disk cam. The moving stage module includes a first linear motion stage, a second linear motion stage and a rotary motion stage. The first linear motion stage is movably disposed on the base, the second linear motion stage is movably disposed on the first linear motion stage, and the rotary motion stage is rotatably disposed on the second linear motion stage. The optical measuring module is disposed on the rotary motion stage and includes a laser-emitting unit and an image-capturing unit. The moving stage module is able to carry the optical measuring module to move together. The computer is able to instruct the rotating chuck carrying the disk cam to rotate, instruct the moving stage module carrying the optical measuring module to move, and instruct the laser-emitting unit emitting a light beam and projecting the light beam onto a profile point on the cam surface of the disk cam. The image-capturing unit is able to receive a local scattering light, which is generated when the light beam is projected onto the profile point, to capture a grayscale measuring image including a profile speckle pattern. The computer is also able to obtain a profile speckle characteristic value of the profile speckle pattern according to the grayscale measuring image and to calculate the surface roughness value of the cam surface at the profile point according to the profile speckle characteristic value.

According to another aspect of the present disclosure, a non-contact and optical measuring method, for measuring a surface roughness value of a cam surface of a disk cam, includes steps as follows: setting a measuring parameter including at least one profile point on the cam surface and a normal direction of the cam surface at the profile point; executing a measuring procedure by an optical measuring module, making a light beam emitting from a laser-emitting unit of the optical measuring module project onto the profile point, making an image-capturing unit of the optical measuring module receive a local scattering light, which is generated when the light beam is projected onto the profile point, to capture at least one grayscale measuring image corresponding to the point, and the grayscale measuring image includes a profile speckle pattern; executing a value obtaining procedure, processing the grayscale measuring image to obtain a profile speckle characteristic value of the profile speckle pattern in the grayscale measuring image; and executing a calculating procedure, substituting the profile speckle characteristic value into a roughness equation to obtain the surface roughness value of the cam surface at the profile point.

BRIEF DESCRIPTION OF THE DRAWINGS

The present disclosure will become more understood from the detailed description given herein below and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1A:
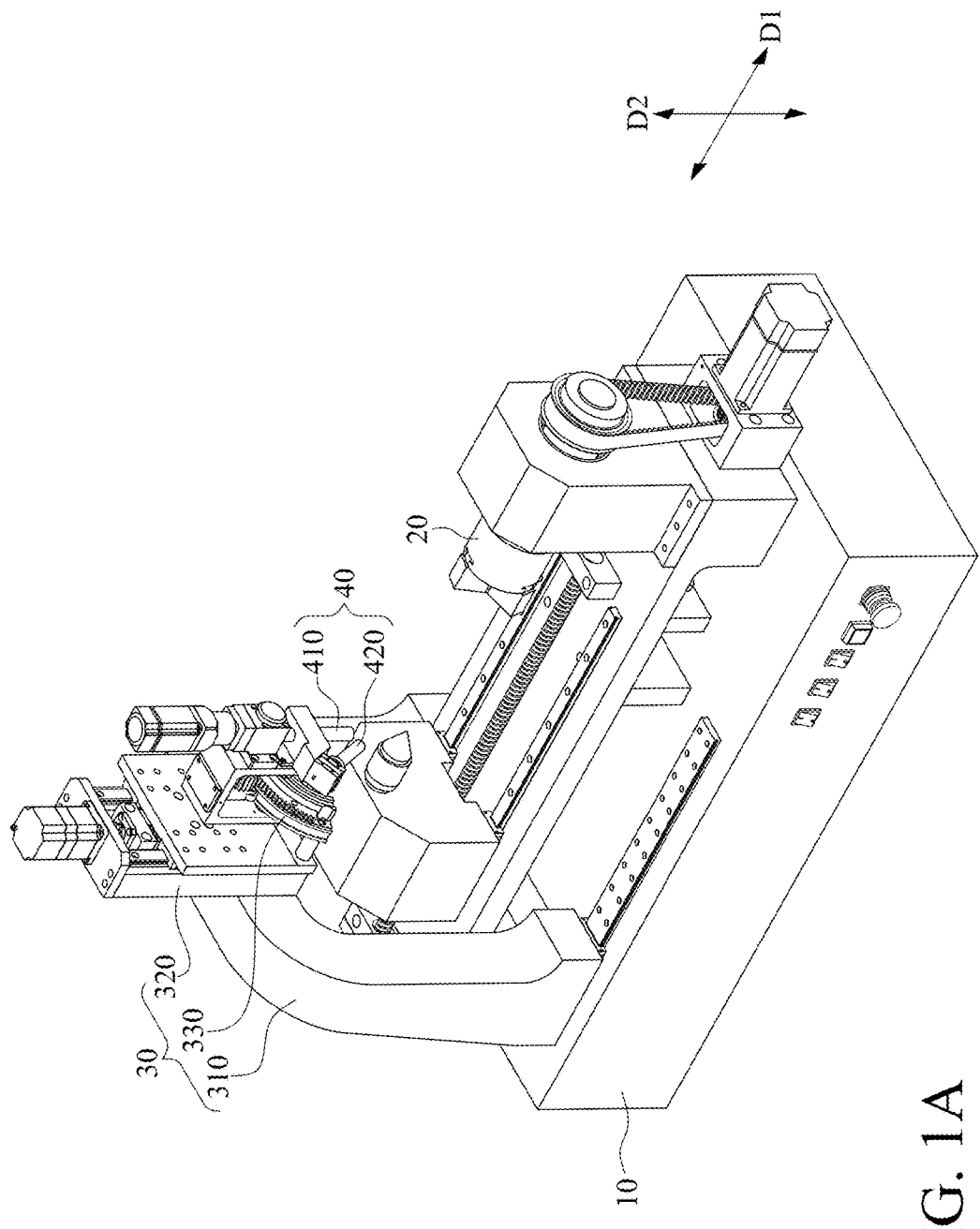
FIG. 1A is a perspective view of a non-contact and optical measuring automation system according to an embodiment of the present disclosure.
Figure 1B:
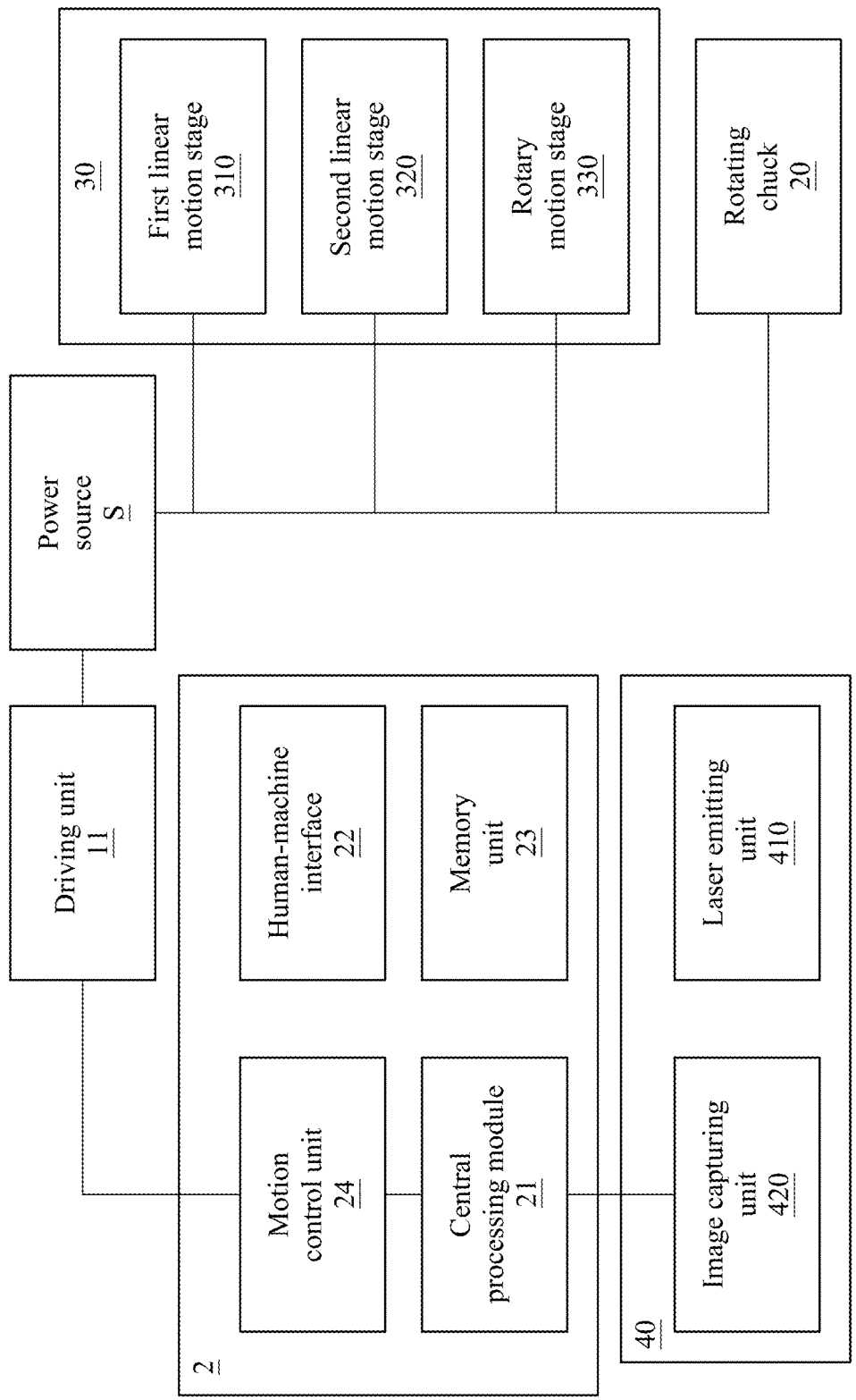
FIG. 1B is a block diagram of the non-contact and optical measuring automation system in FIG. 1A and a computer.
Figure 2:
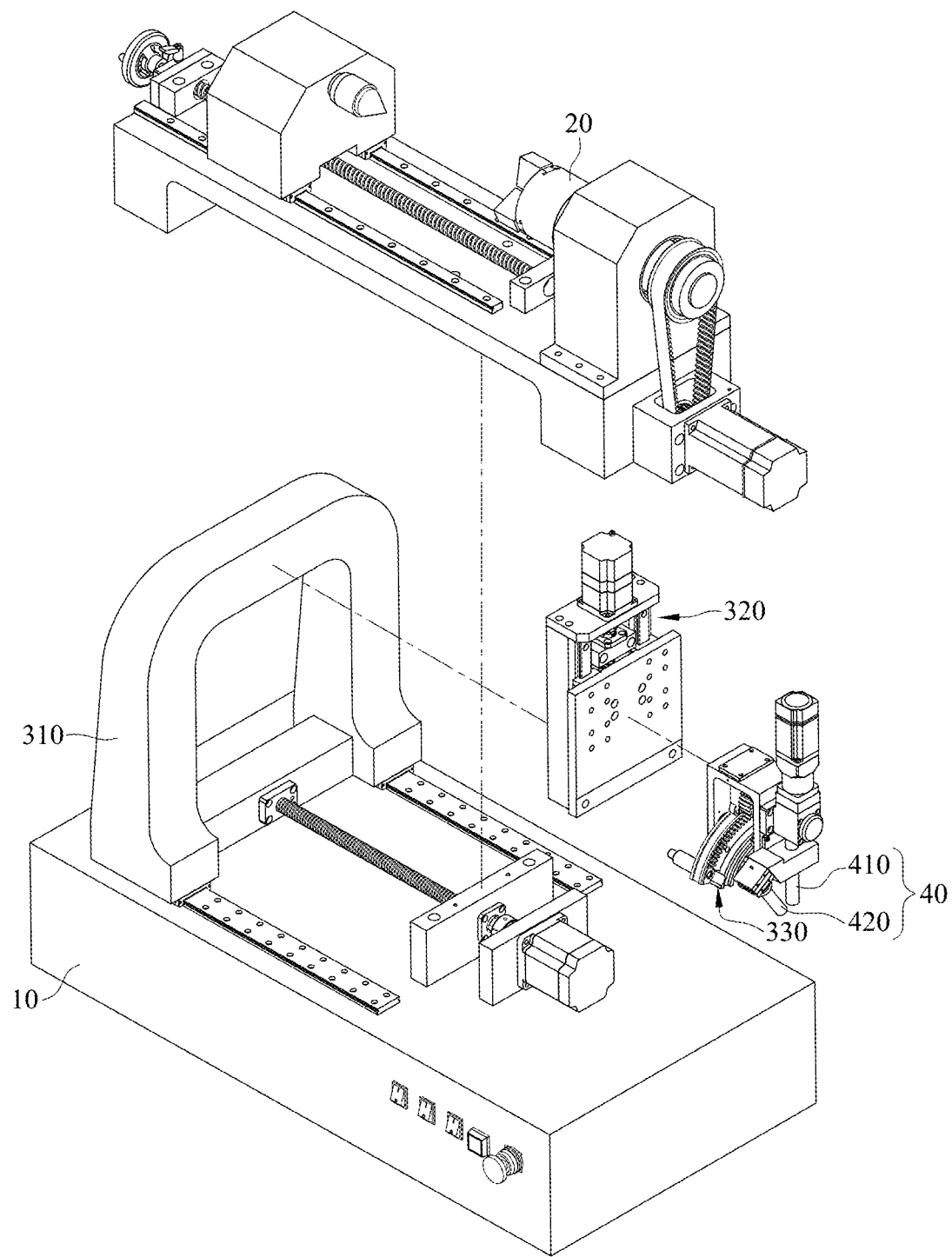
FIG. 2 is an exploded view of the non-contact and optical measuring automation system in FIG. 1A.
Figure 3A:
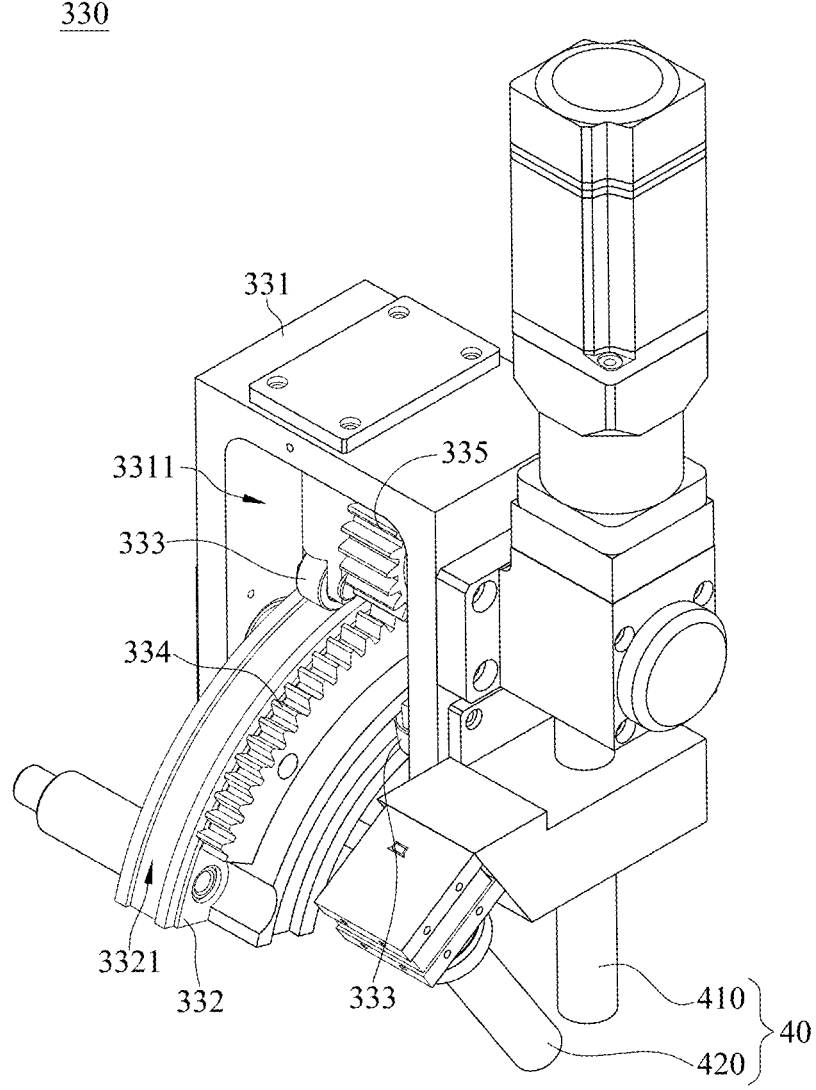
FIG. 3A is a perspective view of a rotary motion stage of a moving stage module of the non-contact and optical measuring automation system in FIG. 2.
Figure 3B:
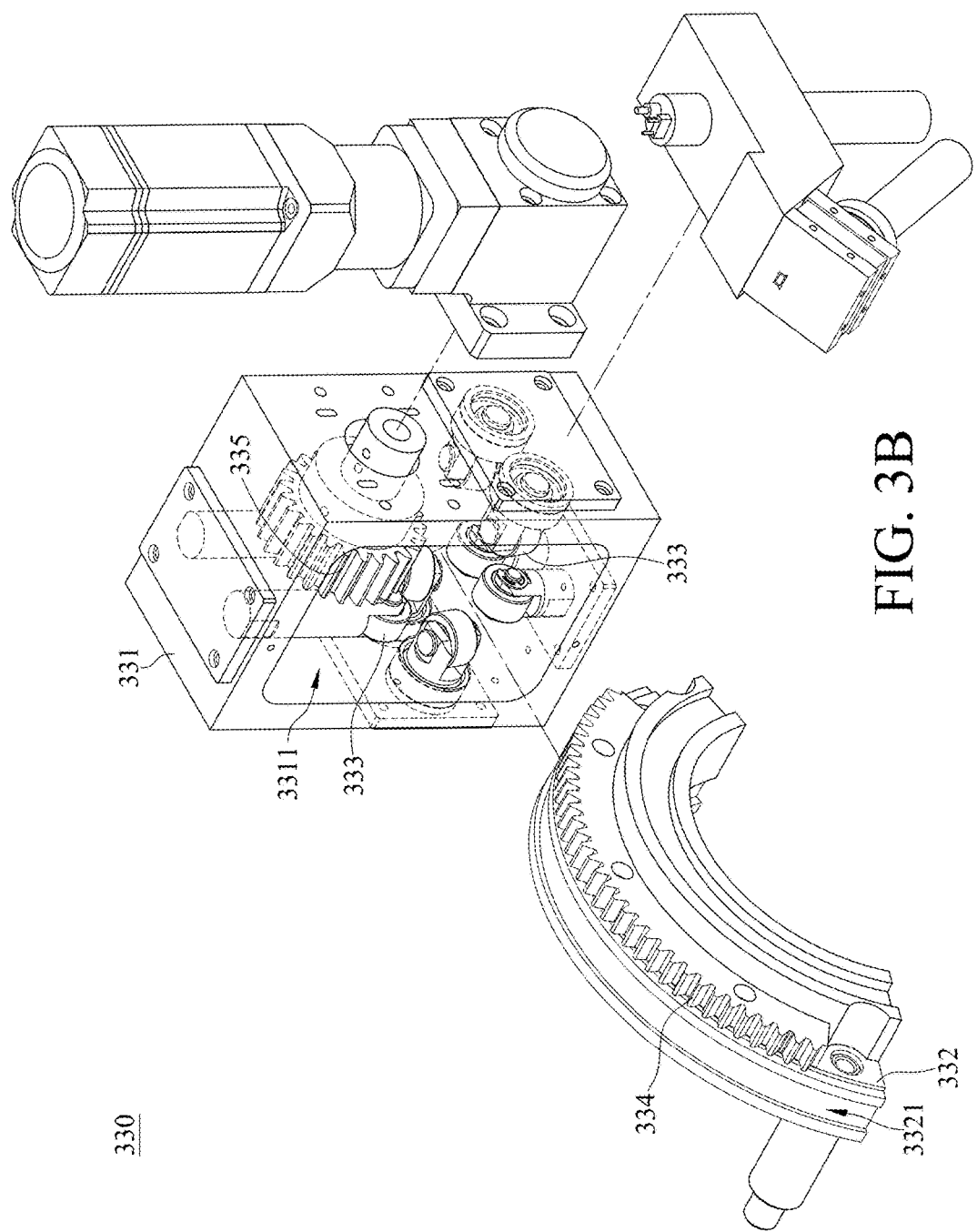
FIG. 3B is an exploded view of the rotary motion stage in FIG. 3A.
Figure 4:
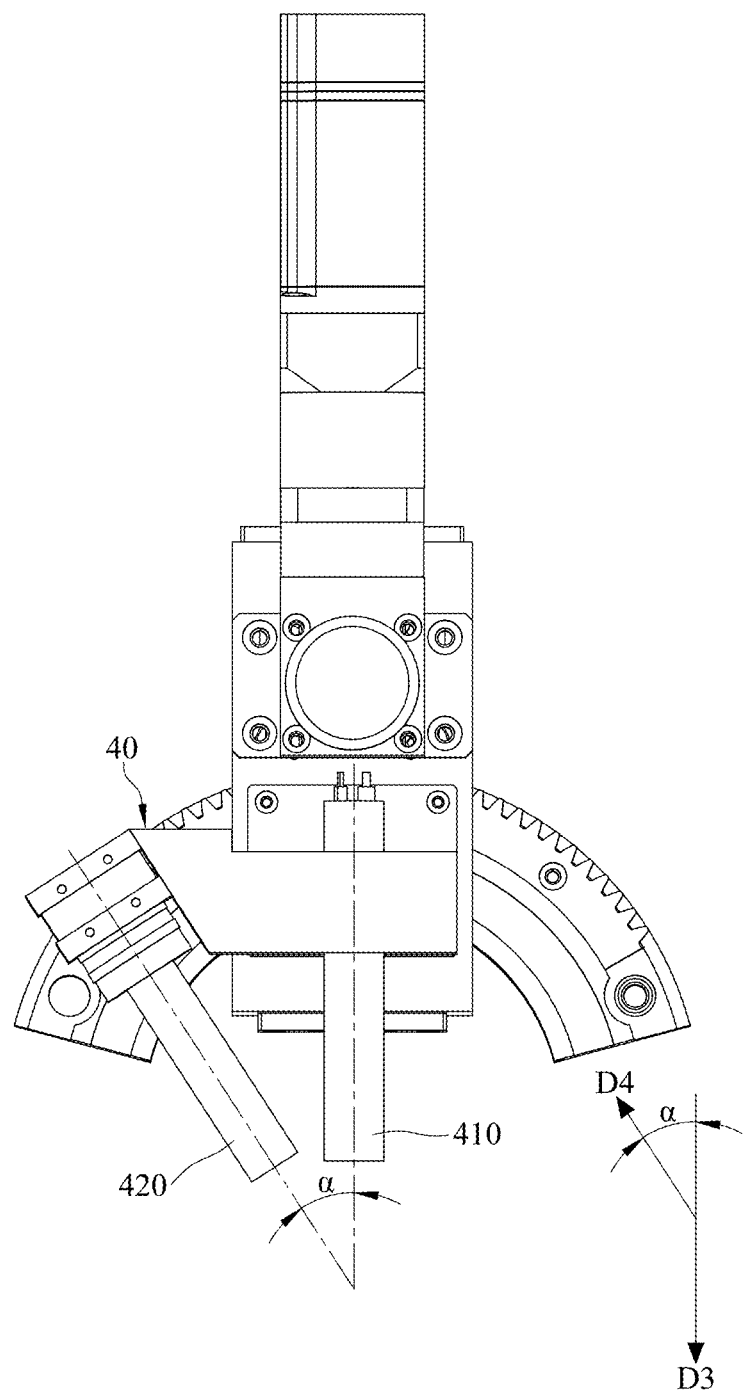
FIG. 4 is a front view of an optical measuring module of the non-contact and optical measuring automation system in FIG. 3A.

Please refer to FIG. 1A to FIG. 4. FIG. 1A is a perspective view of a non-contact and optical measuring automation system according to an embodiment of the present disclosure. FIG. 1B is a block diagram of the non-contact and optical measuring automation system in FIG. 1A and a computer. FIG. 2 is an exploded view of the non-contact and optical measuring automation system in FIG. 1A. FIG. 3A is a perspective view of a rotary motion stage of a moving stage module of the non-contact and optical measuring automation system in FIG. 2. FIG. 3B is an exploded view of the rotary motion stage in FIG. 3A. FIG. 4 is a front view of an optical measuring module of the non-contact and optical measuring automation system in FIG. 3A. In this embodiment, a non-contact and optical measuring automation system 1 is configured to measure the surface roughness value of a disk cam in an automatic and non-contact manner. The non-contact and optical measuring automation system 1 includes a base 10, a rotating chuck 20, a moving stage module 30 and an optical measuring module 40.

The rotating chuck 20 is disposed on the base 10 for clamping the disk cam, and the disk cam is allowed to rotate around a rotational axis of the disk cam. The function of the rotating chuck 20 will be further described hereafter.

The moving stage module 30 includes a first linear motion stage 310, a second linear motion stage 320 and a rotary motion stage 330. The first linear motion stage 310, the second linear motion stage 320 and the rotary motion stage 330 are connected to a power source S including one or more motors. The first linear motion stage 310 is disposed on the base 10, and the first linear motion stage 310 is movable relative to the base 10 in a first direction D1. The second linear motion stage 320 is disposed on the first linear motion stage 310, and the second linear motion stage 320 is movable relative to the first linear motion stage 310 in a second direction D2 which is non-parallel to the first direction D1. In this embodiment, the second direction D2 is orthogonal to the first direction D1.

The rotary motion stage 330 is rotatably disposed on the second linear motion stage 320. In detail, the rotary motion stage 330 includes a rotary carriage 331, a circular rail member 332, a plurality of rollers 333, a segmented spur gear 334 and a pinion gear 335. The circular rail member 332 is disposed on the second linear motion stage 320 and passes through a through slot 3311 of the rotary carriage 331. The circular rail member 332 has a plurality of bearing surfaces 3321 which respectively correspond to the rollers 333. The rollers 333 are rotatably accommodated in the through slot 3311, and the rollers 333 contact the bearing surfaces 3321, respectively, so that the rotary carriage 331 is able to rotate relative to the circular rail member 332. The segmented spur gear 334 is fixed to the circular rail member 332, the pinion gear 335 is disposed on the shaft of the power source S, the power source S is disposed on the rotary carriage 331, and the segmented spur gear 334 is engaged with the pinion gear 335; thus, the relative motions between the segmented spur gear 334, the pinion gear 335 and the rotary carriage 331 are equivalent to a conventional planetary gear train. When the power source S is turned on, the rolling motion of the pinion gear 335 relative to the segmented spur gear 334 simultaneously carries the rotary carriage 331 to rotate relatively to the circular rail member 332, thereby allowing the rotary motion stage 330 to rotate relative to the second linear motion stage 320.

The optical measuring module 40 is disposed on the rotary carriage 331 of the rotary motion stage 330, and the second linear motion stage 320 is able to move the rotary motion stage 330 in a second direction D2 together with the optical measuring module 40. In this embodiment, the optical measuring module 40 includes a laser-emitting unit 410 and an image-capturing unit 420 which are two separated components. The laser-emitting unit 410 is a laser diode module, and the image-capturing unit 420 is a camera including an image sensor and a lens. The image sensor of the image-capturing unit 420, for example, is a complementary metal-oxide-semiconductor (CMOS) or a charge-coupled device (CCD). The lens of the image-capturing unit 420, for example, is a telecentric lens. The laser-emitting unit 410 and the image-capturing unit 420 are disposed on a lateral side of the rotary carriage 331 of the rotary motion stage 330. The laser-emitting unit 410 can emit a light beam in an emitting direction D3, and the light beam is projected onto the surface of a tested object so as to generate scattering light. Some scattering light travels along a receiving direction D4 to project onto and be received by the image-capturing unit 420. In this embodiment, there is a constant acute angle α subtended between the emitting direction D3 and the receiving direction D4, and the constant acute angle α is ranged between 30.0 degrees to 60.0 degrees. Furthermore, the laser-emitting unit 410 emits the light beam along the emitting direction D3 with an output power of the light beam being less than or equal to 10 milliwatts (mW) in this embodiment.

In the non-contact and optical measuring automation system 1, the rotating chuck 20, the moving stage module 30 and the optical measuring module 40 can be electrically connected to a computer 2. More specifically, the computer 2, for example, is an electronic device with a function of data processing, such as a desktop computer. The computer 2 includes a central processing module 21, a human-machine interface 22, a memory unit 23 and a motion control unit 24, and there is a driving unit 11 disposed in the base 10. The central processing module 21 of the computer 2 is electrically connected to the driving unit 11 in the base 10 by the motion control unit 24 so as to instruct the power source S driving the rotating chuck 20 to clamp and rotate the disk cam, driving the first linear motion stage 310 of the moving stage module 30 to move relatively to the base 10, driving the second linear motion stage 320 to move relatively to the first linear motion stage 310, and driving the rotary motion stage 330 to rotate relatively to the second linear motion stage 320. In this embodiment, the first linear motion stage 310 and the second linear motion stage 320 are driven by stepping motors, while the rotating chuck 20 and the rotary motion stage 330 are driven by servo motors. Moreover, both the first linear motion stage 310 and the second linear motion stage 320 include a linear encoder therein, and each of the servo motors of the rotating chuck 20 and the rotary motion stage 330 includes a rotary encoder. The linear encoders detect the moving positions of the first linear motion stage 310 and the second linear motion stage 320, and return the moving positions to the motion control unit 24 so as to execute a closed-loop motion control thereof. The rotary encoders detect the rotating angles of the rotating chuck 20 and the rotary motion stage 330, and return the rotating angles to the motion control unit 24 so as to execute the closed-loop motion control thereof. Thus, the positioning accuracy, which is needed during the measurement, is achieved by the non-contact and optical measuring automation system 1. The computer 2 also instructs the image-capturing unit 420 of the optical measuring module 40 receiving local scattering light, which is generated when the light beam is projected onto the tested object by the laser-emitting unit 410, thereby capturing an image which is able to be displayed on the human-machine interface 22.

Figure 5A:
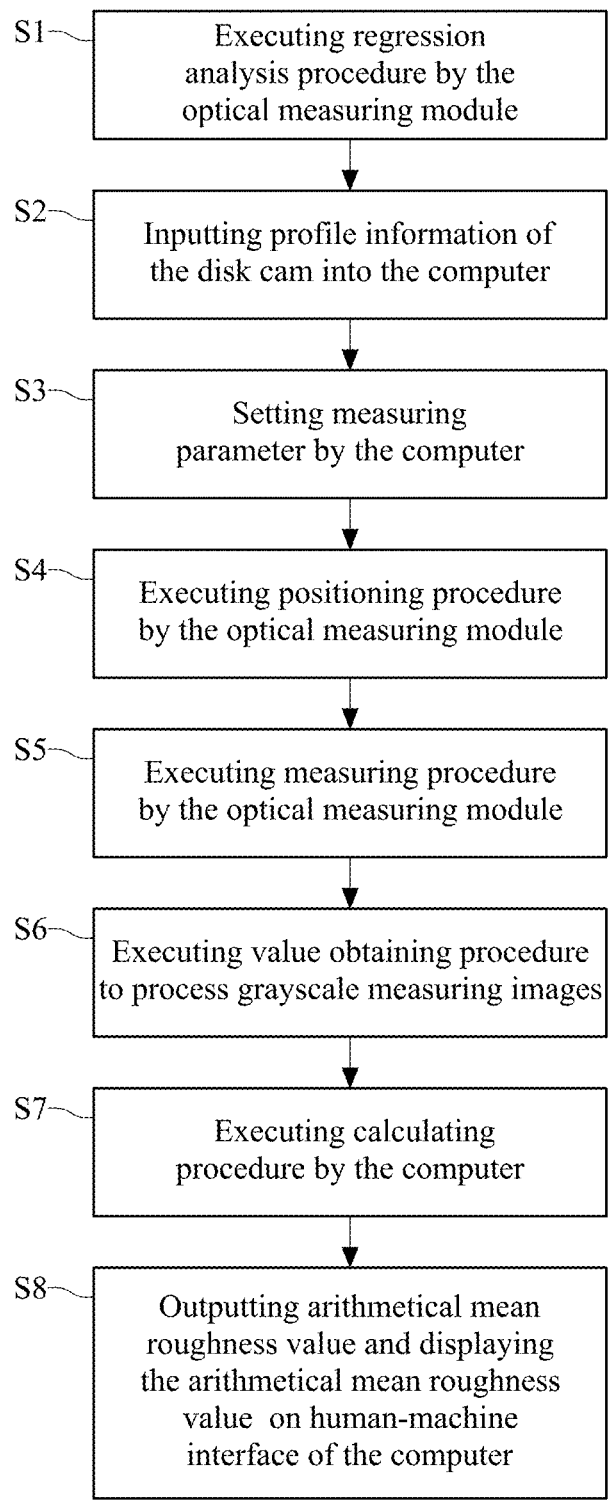
FIG. 5A is a flowchart of a non-contact and optical measuring method according to an embodiment of the present disclosure.
Figure 5B:
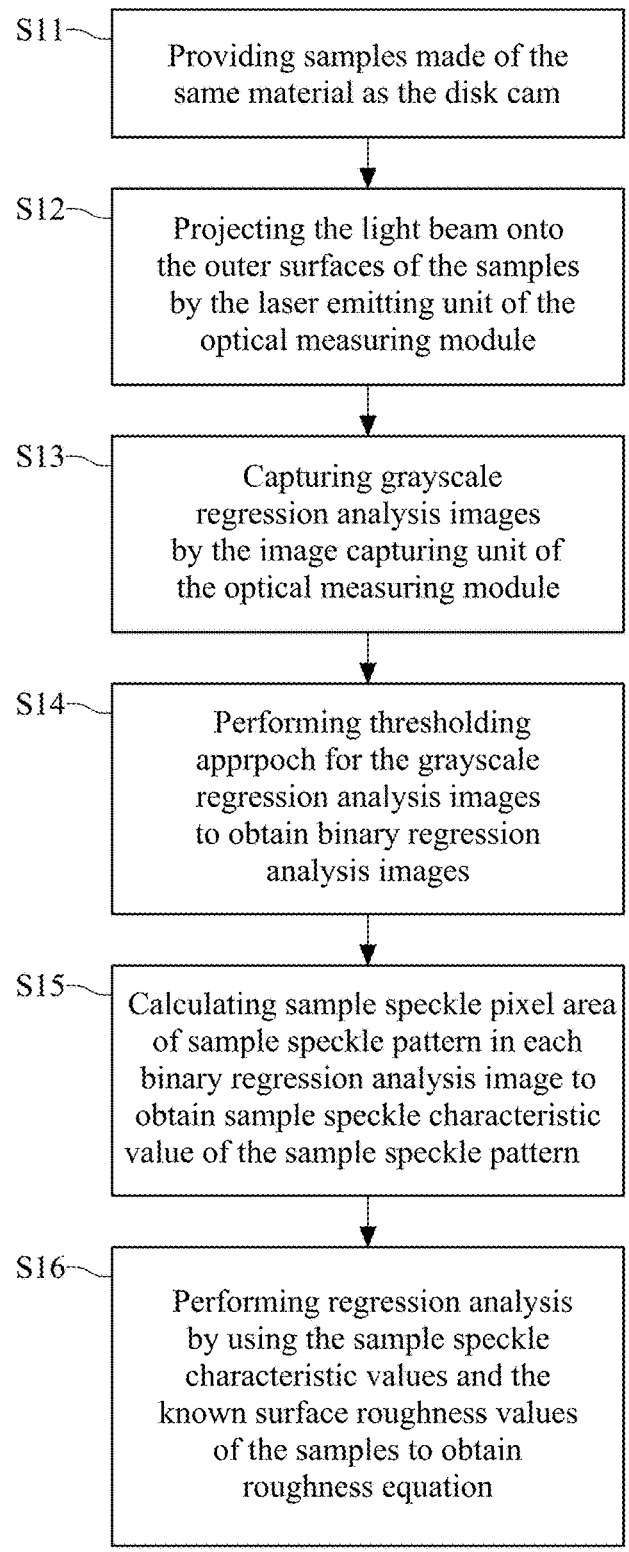
FIG. 5B is a flowchart of a regression analysis procedure of the non-contact and optical measuring method in FIG. 5A.
Figure 5C:
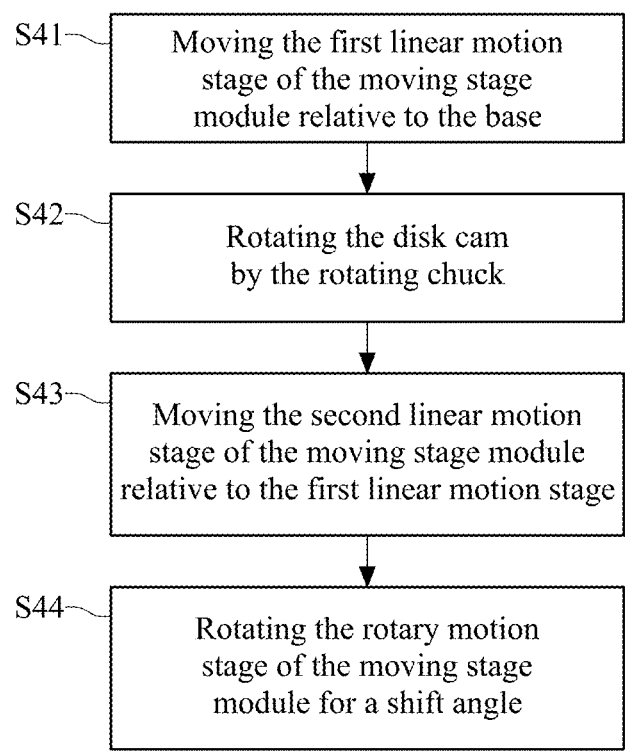
FIG. 5C is a flowchart of a positioning procedure of the non-contact and optical measuring method in FIG. 5A.
Figure 5D:
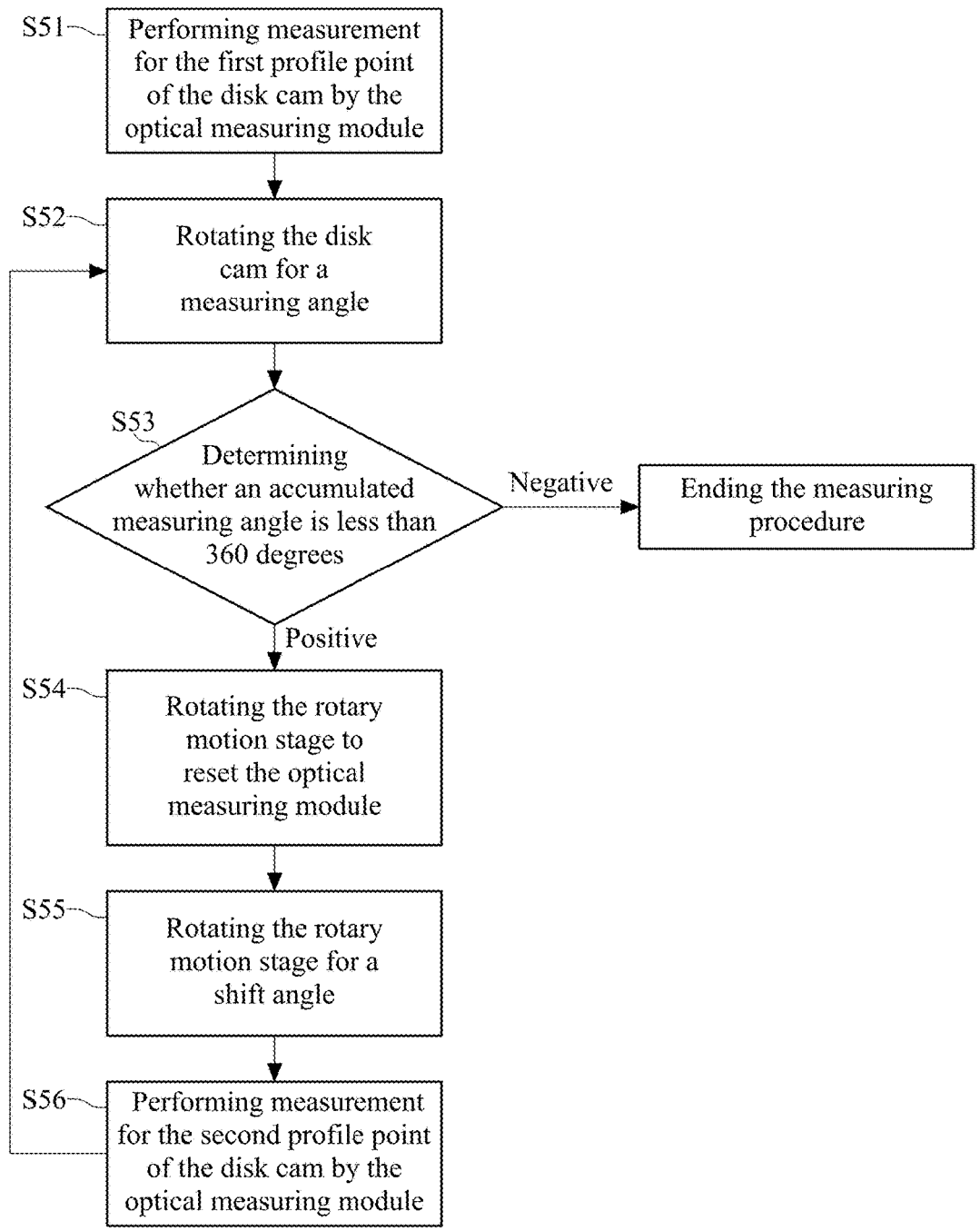
FIG. 5D is a flowchart of a measuring procedure of the non-contact and optical measuring method in FIG. 5A.
Figure 5E:
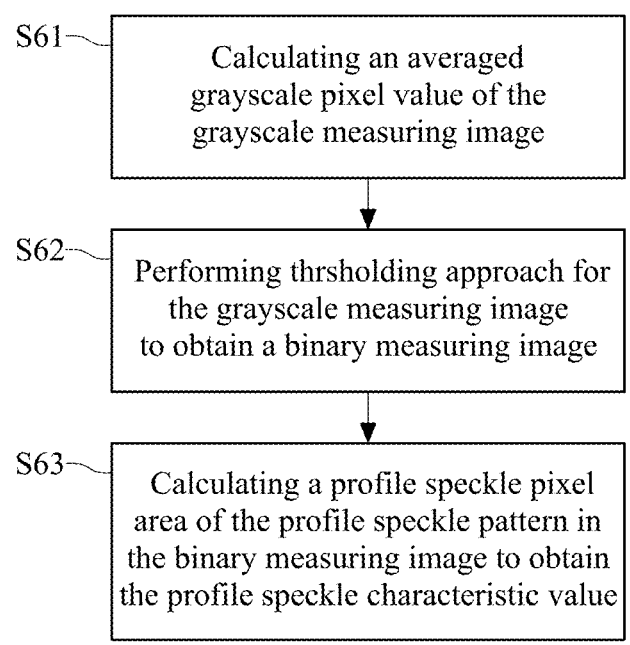
FIG. 5E is a flowchart of a value obtaining procedure of the non-contact and optical measuring method in FIG. 5A.

The following describes the usage of the non-contact and optical measuring automation system 1 in this embodiment to measure the surface roughness value of the disk cam. FIG. 5A is a flowchart of a non-contact and optical measuring method according to an embodiment of the present disclosure. FIG. 5B is a flowchart of a regression analysis procedure of the non-contact and optical measuring method in FIG. 5A. FIG. 5C is a flowchart of a positioning procedure of the non-contact and optical measuring method in FIG. 5A. FIG. 5D is a flowchart of a measuring procedure of the non-contact and optical measuring method in FIG. 5A. FIG. 5E is a flowchart of a value obtaining procedure of the non-contact and optical measuring method in FIG. 5A. FIG. 6A to FIG. 6H are schematic views of measuring the surface roughness values of a disk cam by the non-contact and optical measuring automation system in FIG. 1. As shown in FIG. 5A, the non-contact and optical measuring method in this embodiment includes steps S1 to S8. Moreover, as shown in FIG. 6B, before starting the measurement, a disk cam 50 is clamped by the rotating chuck 20 of the non-contact and optical measuring automation system 1.

The disk cam 50 in this embodiment is adapted to a cam mechanism with an offset translating roller follower, but the disclosure is not limited thereto. In some embodiments, the disk cam measure by the non-contact and optical measuring automation system 1 is adapted to a cam mechanism with a translating flat-faced follower or a cam mechanism with an oscillating roller follower, wherein either a single disk cam or a conjugate disk cam is applied in the said cam mechanism. Furthermore, the surface roughness value of the disk cam 50 measured in this embodiment is the arithmetical mean roughness (Ra), but the disclosure is not limited thereto. In some embodiments, the surface roughness value, measured by the non-contact and optical measuring automation system 1, is the maximum roughness depth (Ry) or the ten point mean roughness (Rz).

Firstly, the step S1 is executed. A regression analysis procedure is executed by the optical measuring module 40 to obtain a roughness equation, before the surface roughness value of the disk cam 50 is measured. As shown in FIG. 5B, the step S1 includes steps S11 to S16.

The step S11 is executed firstly. A plurality of samples 60 is provided, and the samples 60 are made of the same material as the disk cam 50. Each sample 60 has a flat or cylindrical outer surface 610; in other words, the outer surfaces 610 of the samples 60 have more than two curvatures, which are different from each other so as to meet the requirement of the curvature varying range of the disk cam 50. The outer surfaces 610 of the samples 60 also have different arithmetical mean roughness values. In this embodiment, both the disk cam 50 and the samples 60 are made of SUS304 stainless steel, but the disclosure is not limited thereto.

Figure 6A:
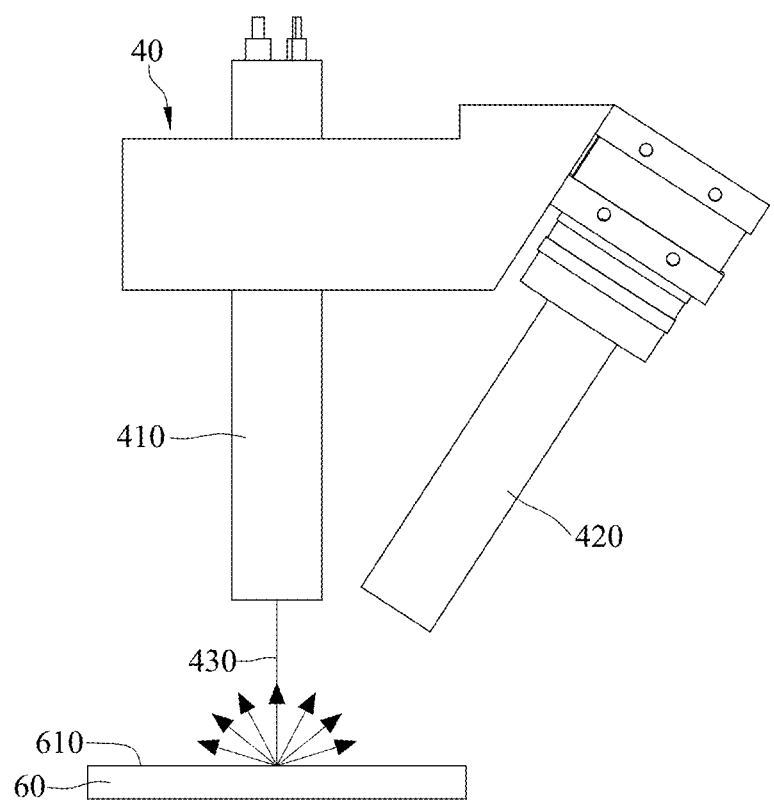
FIG. 6A to FIG. 6H are schematic views of measuring the surface roughness values of a disk cam by the non-contact and optical measuring automation system in FIG. 1A.
Figure 6B:
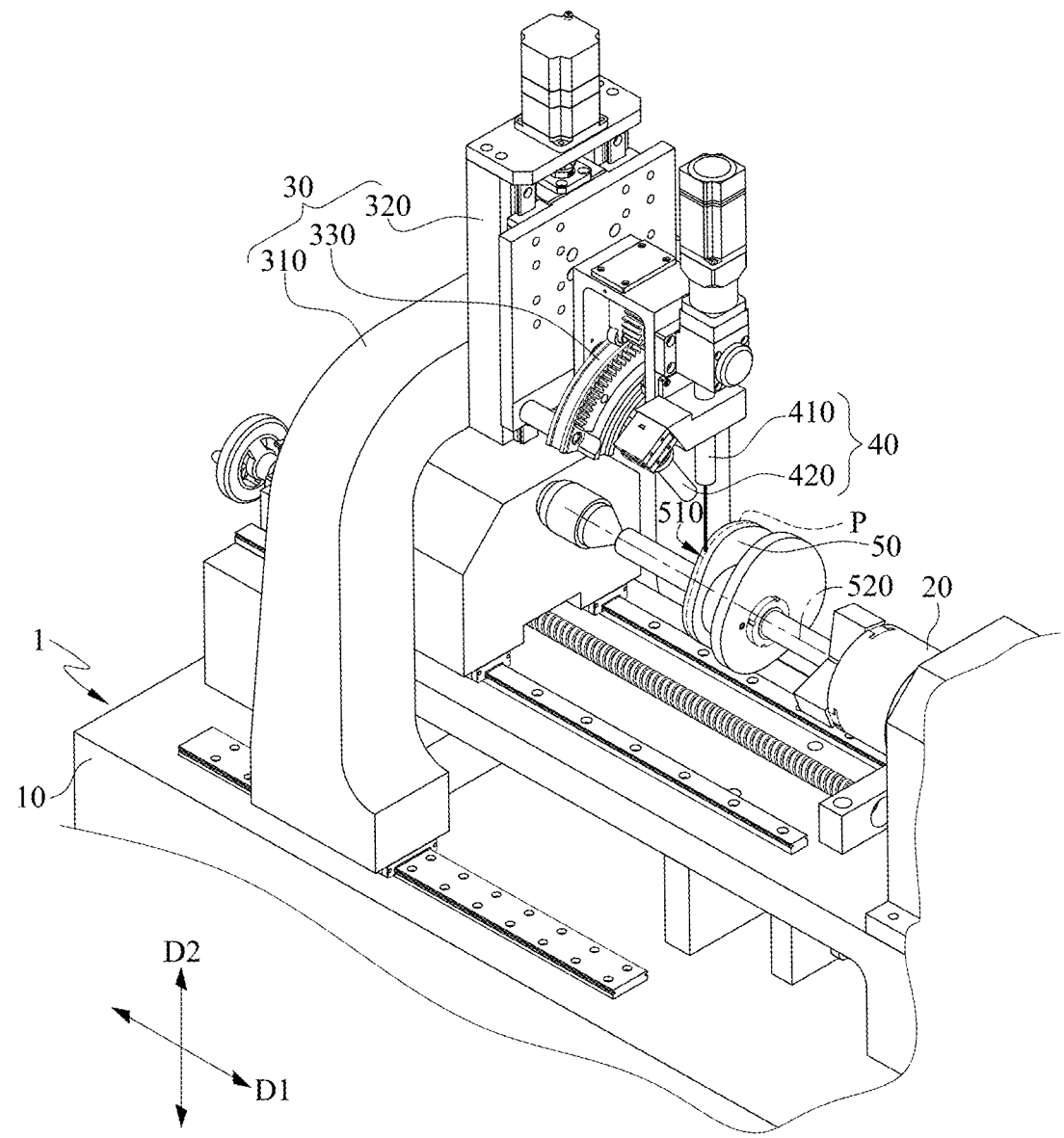

As shown in FIG. 6A, the step S12 is then executed. The laser-emitting unit 410 of the optical measuring module 40 emits a light beam 430, and the light beam 430 travels in a direction normal to the outer surface 610. The light beam 430 is projected onto the outer surface 610, and the laser scattering phenomena is then occurred to generate a plurality of scattering lights.

Figure 7A:
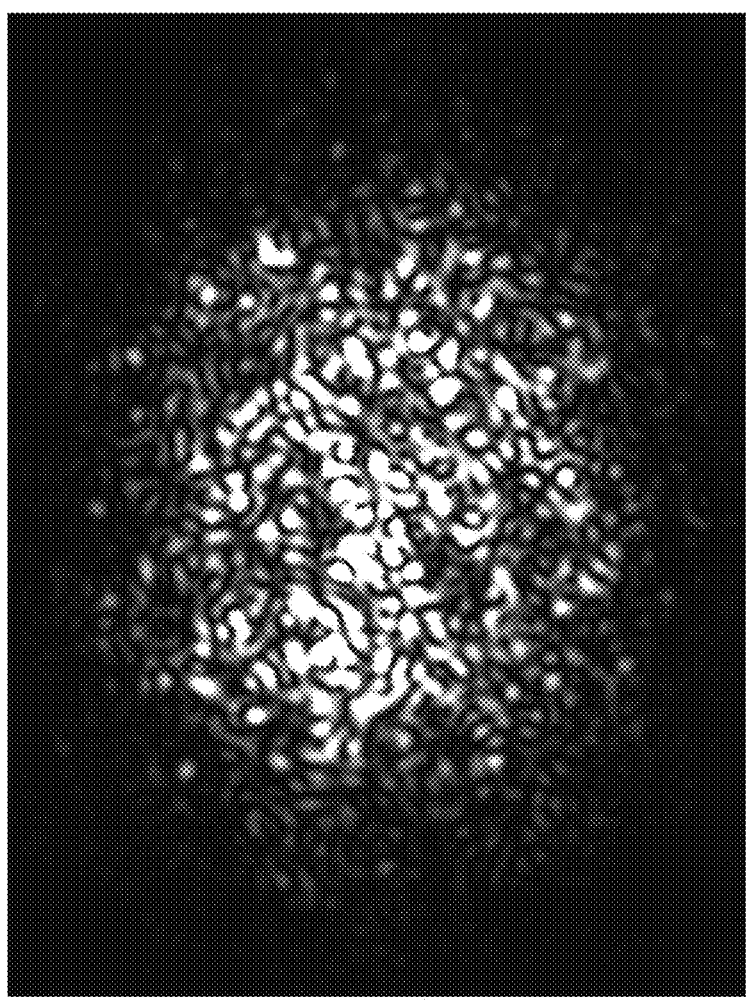
FIG. 7A is a grayscale image including a speckle pattern.

The step S13 is then executed. The image-capturing unit 420 of the optical measuring module 40 receives a local scattering light, which is generated when the light beam 430 is projected onto the outer surface 610, to capture a plurality of grayscale regression analysis images. Each grayscale regression analysis image includes a sample speckle pattern, and the sample speckle patterns respectively correspond the samples 60. The sample speckle pattern results from laser speckles formed by the laser scattering phenomena. FIG. 7A is a grayscale image including a speckle pattern, which can represent a grayscale regression analysis image including a sample speckle pattern.

The step S14 is then executed. A thresholding approach is performed to digitally process the grayscale regression analysis images to obtain a plurality of binary regression analysis images. In detail, each grayscale regression analysis image (FIG. 7A) captured in the step S13 can be digitalized to obtain a pixel value of each pixel in the grayscale regression analysis image (the pixel value ranges from 0 to 255) and an averaged grayscale pixel value can be calculated. The thresholding approach is performed, with the averaged grayscale pixel value as a threshold value, to obtain the binary regression analysis image (the pixel value ranges from 0 to 1) of each grayscale regression analysis image. The averaged grayscale pixel value of the grayscale regression analysis image is calculated from the following equation:

$$k = \sum_{i=1}^{m} \sum_{j=1}^{n} \frac{g_{ij}}{(m \times n)} \qquad \text{Equation (1)}$$

Figure 7B:
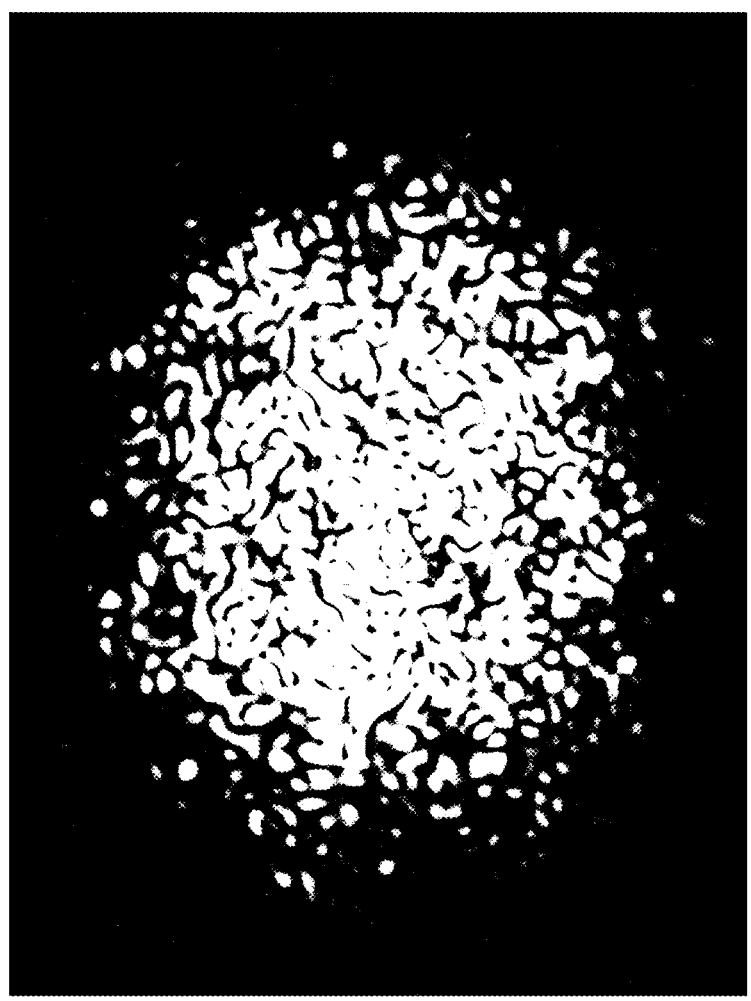
FIG. 7B is a binary image of the grayscale image in FIG. 7A.

In equation (1), k represents the averaged grayscale pixel value of the grayscale regression analysis image, m represents the number of pixels in width of the grayscale regression analysis image, n represents the number of pixels in height of the grayscale regression analysis image, and $g_{ij}$ represents the pixel value at the coordinates (i, j) of the grayscale regression analysis image. FIG. 7B is a binary image of the grayscale image in FIG. 7A, which can represent a binary regression analysis image generated by performing the thresholding approach for a grayscale regression analysis image with a threshold value of 44.676. In this embodiment, the sample speckle pattern has higher pixel value so that a region in the binary image (FIG. 7B), where the sample speckle pattern is located, is white, and the rest region (i.e. the background) in the binary image is black.

The step S15 is then executed. A sample speckle pixel area of the sample speckle pattern in each binary regression analysis image is calculated to obtain a sample speckle characteristic value of the sample speckle pattern. In detail, the sample speckle pixel area is calculated from the following equation:

$$A_b = \left(\sum_{i=1}^{m}\sum_{j=1}^{n} b_{ij}\right) \times A_u \qquad \text{Equation (2)}$$

In equation (2), $A_b$ represents the sample speckle pixel area (the area in the binary regression analysis image occupied by the sample speckle pattern, pixel$^2$) of the sample speckle pattern, m represents the number of pixels in width of the binary regression analysis image, n represents the number of pixels in height of the binary regression analysis image, $b_{ij}$ represents the pixel value at the coordinates (i, j) of the binary regression analysis image, and $A_u$ represents the area of each pixel (that is, one pixel$^2$) in the binary regression analysis image. The sample speckle characteristic value is then calculated from the following equation:

$$\sigma = A_b \times T \qquad \text{Equation (3)}$$

In equation (3), $\sigma$ represents the sample speckle characteristic value ($\mu m^2$), T represents a scale conversion value which is a ratio of the physical area of the image captured by the image-capturing unit 420 to the pixel area of said image ($\mu m^2$/pixel$^2$). Thus, $\sigma$ is equal to the physical area of the sample speckle pattern. When FIG. 7B is regarded as a binary regression analysis image, an area of 1275573 pixel$^2$ in FIG. 7B, which is occupied by the sample speckle pattern, is the sample speckle pixel area. The sample speckle pixel area is multiplied by the scale conversion value of 0.0189 $\mu m^2$/pixel$^2$ to obtain a sample speckle physical area of about 24108.33 $\mu m^2$, and this sample speckle physical area is the sample speckle characteristic value of the sample speckle pattern in FIG. 7B. In this embodiment, a region of FIG. 7B, where the sample speckle pattern is located, is white so that the pixel value in this region is equal to one (that is, $b_{ij}=1$); the rest region of FIG. 7B is black so that the pixel value in this region is equal to zero (that is, $b_{ij}=0$). When the outer surface 610 of the sample 60 is rougher, more scattering lights will be generated by the light beam 430 projected onto the outer surface 610, the distribution of the local scattering light will also be broader, and thus the sample speckle characteristic value obtained in step S15 will be greater.

The sample speckle characteristic value in this embodiment is obtained by multiplying the sample speckle pixel area by the scale conversion value, but the disclosure is not limited thereto. In some cases, the sample speckle characteristic value of the sample speckle pattern in FIG. 7B is a ratio of the sample speckle pixel area to a total pixel area of the binary regression analysis image.

Figure 7C:
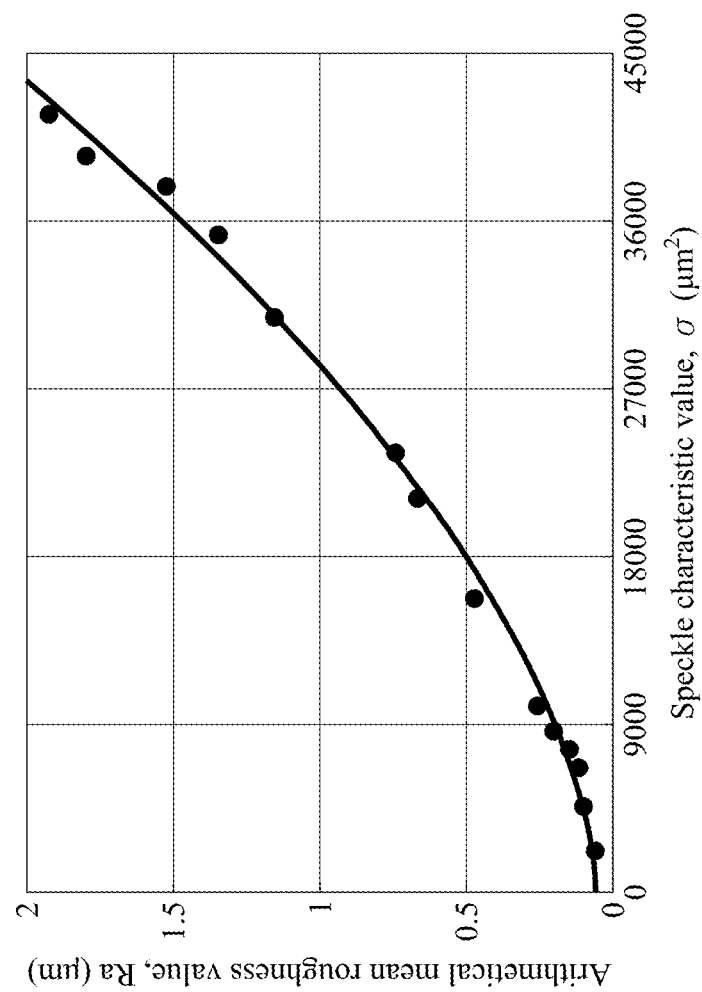
FIG. 7C is a curve diagram representing a relation between a speckle characteristic value of the speckle pattern and the surface roughness value.

The step S16 is then executed. A regression analysis is performed to analyze the sample speckle characteristic values of the sample speckle patterns and the known surface roughness values of the samples 60 to obtain the roughness equation. The roughness equation is a function between the speckle characteristic value and the surface roughness value. FIG. 7C is a curve diagram representing a relation between speckle characteristic values of the speckle patterns and the surface roughness values, wherein y-axis represents the sample speckle characteristic value, and x-axis represents the arithmetical mean roughness of the outer surface 610. In this embodiment, the roughness equation is a non-linear function as follows:

$$Ra = (3.591 \times 10^{-8}) \times \sigma^{1.66} + 0.05 \qquad \text{Equation (4)}$$

In equation (4), Ra represents the known surface roughness value ($\mu m$) of the outer surface 610, and $\sigma$ represents the sample speckle characteristic value obtained in the step S15.

After finishing the step S1, the step S2 is executed. A piece of profile information of the disk cam 50 is inputted into the computer 2. In this embodiment, the profile information includes a radius of the base circle of the disk cam 50, a roller radius of the cam mechanism including the disk cam 50, an offset of the roller of the cam mechanism including the disk cam 50, a theoretical thickness of the disk cam 50, specified follower motion equations of the cam mechanism including the disk cam 50, parametric vector equations of the cam profile of the disk cam 50, the coordinates of the cam profile of the disk cam 50, the coordinate of the rotational center of the disk cam 50, shift angles between radial and normal directions corresponding to the cam profile of the disk cam 50, and so on. The above shift angle between radial and normal directions is defined as the angle subtended between the radial and normal vectors corresponding to one profile point of the disk cam 50. The magnitude of a shift angle, as that of a conventional pressure angle, varies with the position of different cam profile point (reference source of the definition of a shift angle: Wen-Tung Chang, *Analysis of Mechanical Errors in Planar Cam Mechanisms and Its Applications*, Ph.D. Dissertation, Department of Power Mechanical Engineering, National Tsing Hua University, Hsinchu, Taiwan, 2007, pp. 42-44.).

Afterwards, the step S3 is executed. A measuring parameter is set by the computer 2. In this embodiment, the measuring parameter includes the roughness equation obtained in the step S16, a cross-section P to be measured, a first profile point $O_1$ on a cam surface 510 of the disk cam 50 and a second profile point $O_2$ on the cam surface 510 thereof. The cross-section P to be measured is a theoretical plane in an axial direction of the disk cam 50, and the cross-section P to be measured is perpendicular to a rotational axis 520 of the disk cam 50. Both the first profile point $O_1$ and the second profile point $O_2$ are located on the cross-section P to be measured. In this embodiment, the first profile point $O_1$ and the second profile point $O_2$ of the measuring parameter are two different coordinates of the cam profile of the disk cam 50, and the profile points can be obtained by inputting values of the coordinates into the computer 2.

The step S4 is then executed. The computer 2 instructs the non-contact and optical measuring automation system 1 executing a positioning procedure to align the optical measuring module 40 with the cross-section P to be measured and to locate the optical measuring module 40 at a default standby position before the measurement begins. As shown in FIG. 5C, in this embodiment, the step S4 includes steps S41 to S44.

As shown in FIG. 6B, the step S41 is executed firstly. The computer 2 instructs the first linear motion stage 310 of the moving stage module 30 moving relative to the base 10, so as to carry the second linear motion stage 320, the rotary motion stage 330 and the optical measuring module 40 to simultaneously move to a position above the disk cam 50 in the first direction D1, thereby aligning the optical measuring module 40 with the cross-section P to be measured. In this embodiment, the first direction D1 is parallel to the rotational axis 520 of the disk cam 50. Furthermore, as shown in FIG. 6D, when the step S41 is finished, the emitting direction D3 of the light beam 430 emitted from the optical measuring module 40 passes through the rotational axis 520 of the disk cam 50 and is parallel to the second direction D2.

Figure 6C:
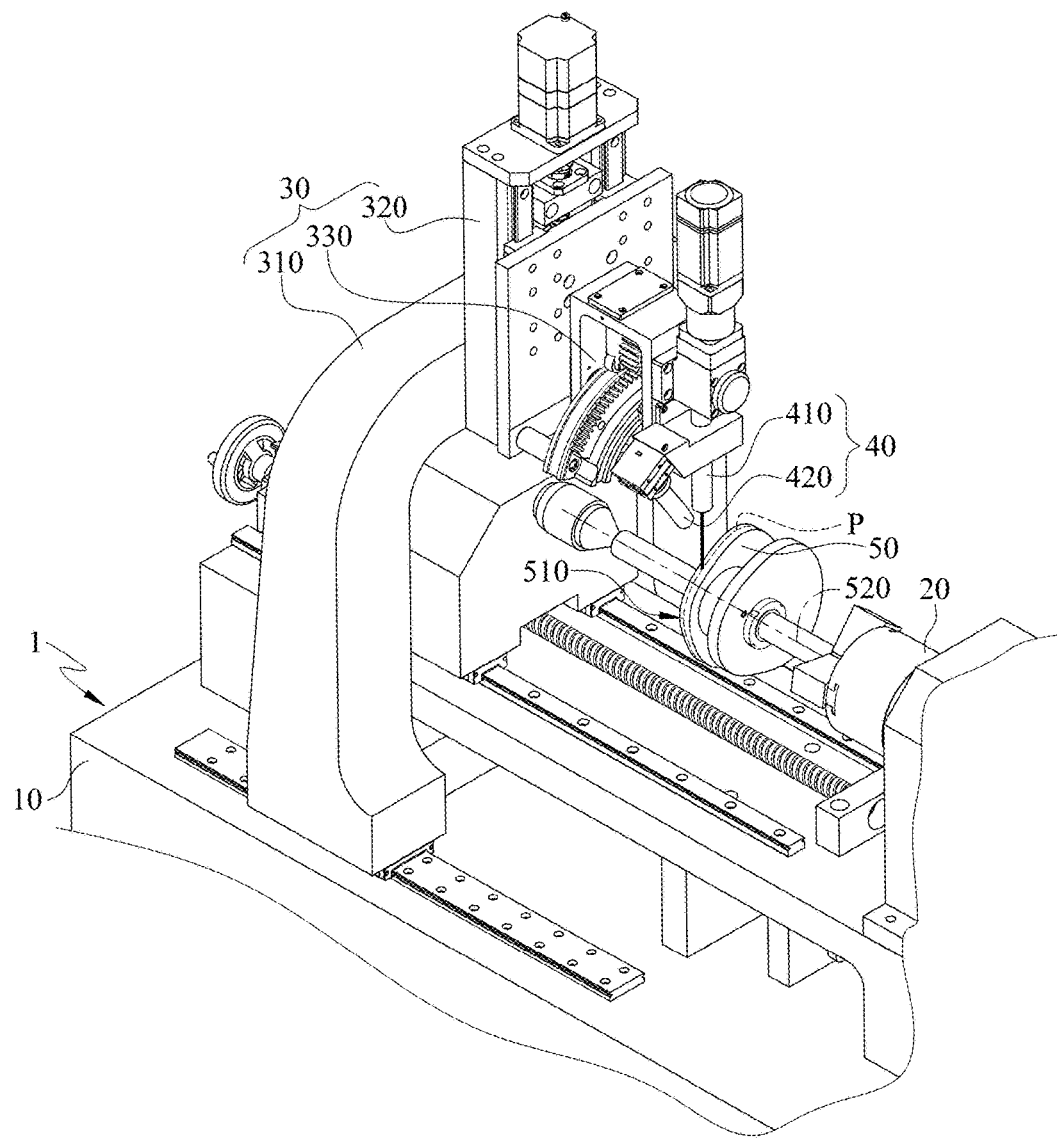
Figure 6D:
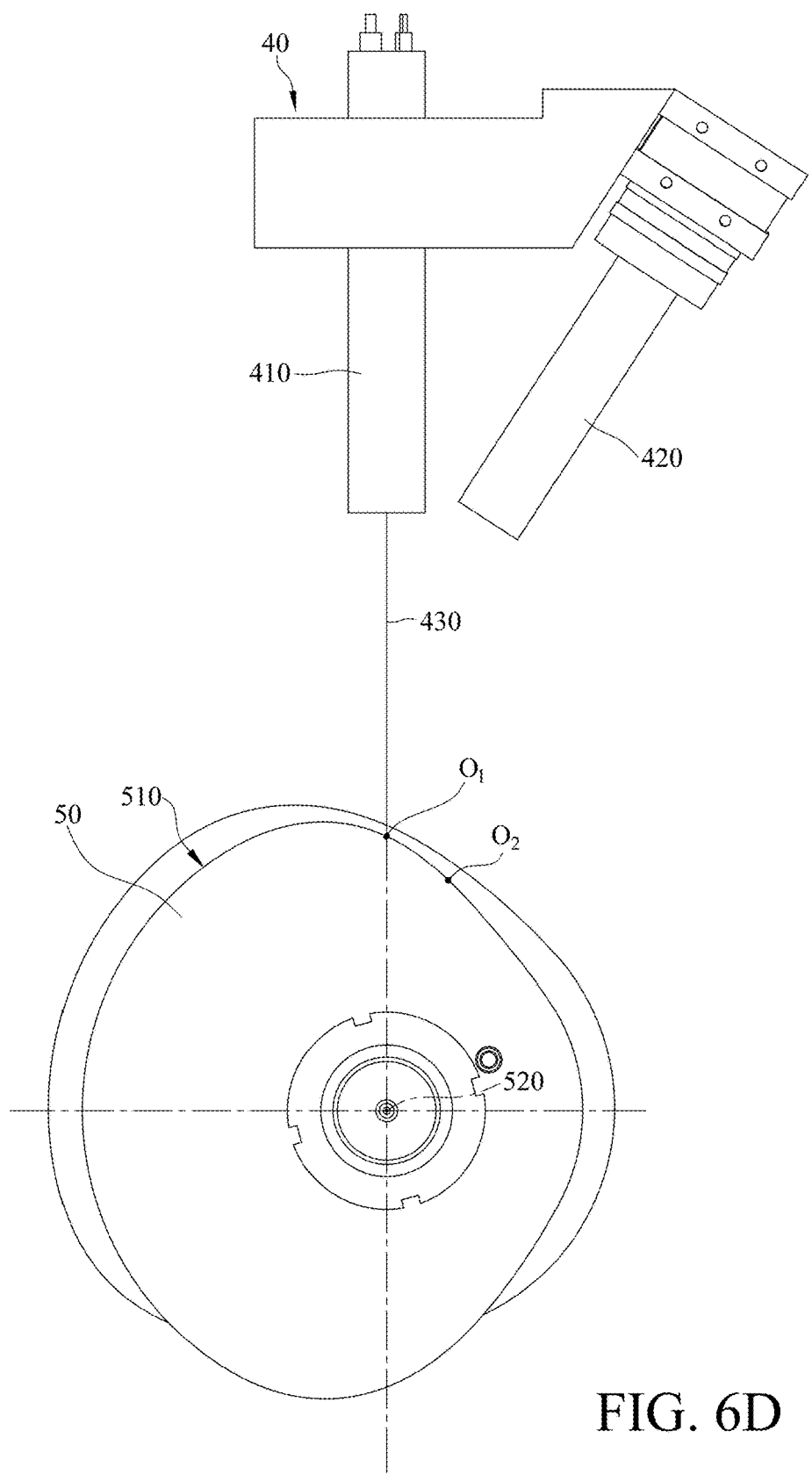

As shown in FIG. 6C and FIG. 6D, the step S42 is executed afterward. The computer 2 instructs the rotating chuck 20 rotating the disk cam 50 to target the laser-emitting unit 410 of the optical measuring module 40 at the first profile point $O_1$.

Figure 6E:
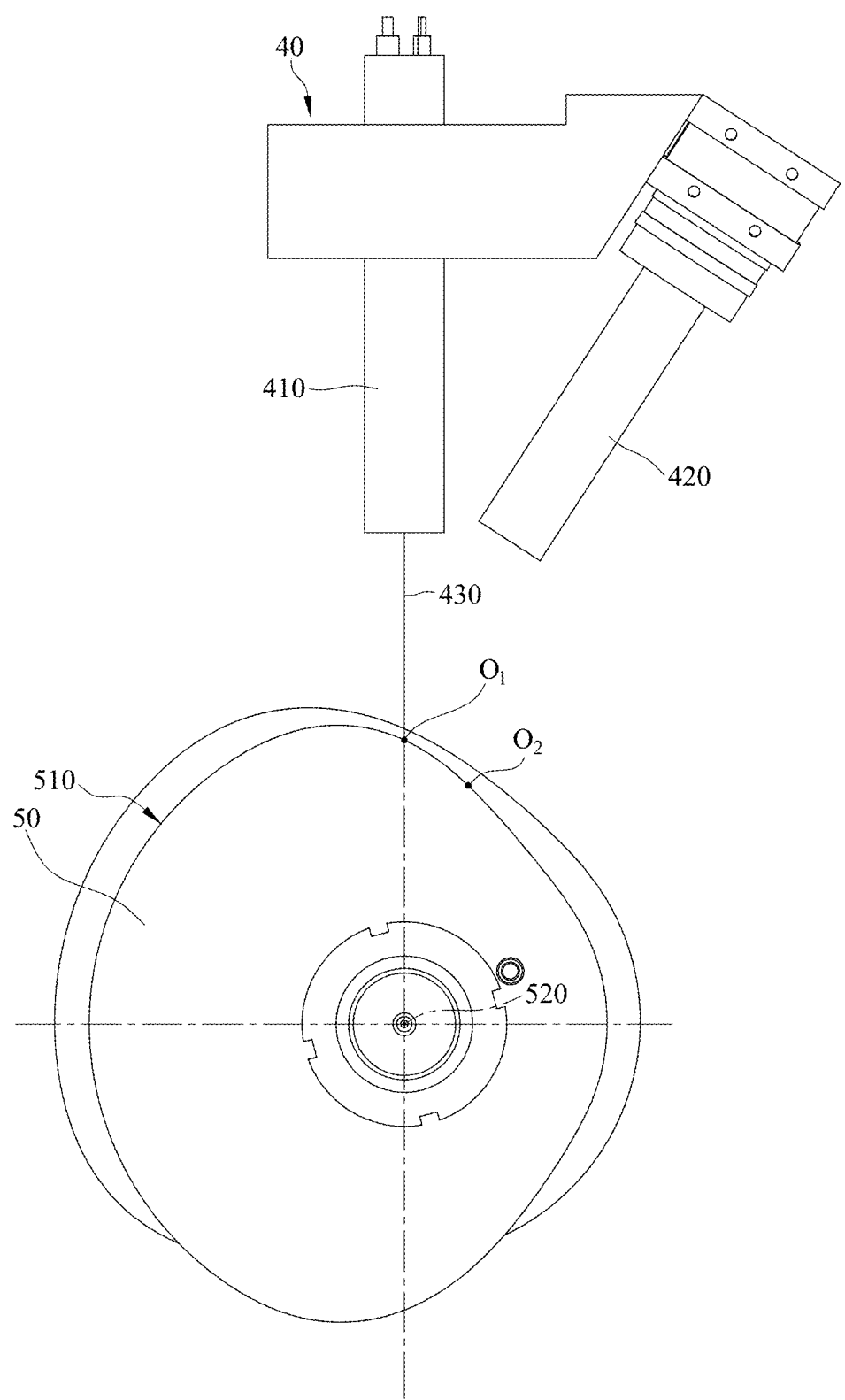

As shown in FIG. 6E, the step S43 is then executed. The computer 2 instructs the second linear motion stage 320 of the moving stage module 30 moving relative to the first linear motion stage 310, so as to carry the rotary motion stage 330 and the optical measuring module 40 to simultaneously move close to or away from the disk cam 50 along the second direction D2, thereby adjusting a distance between the optical measuring module 40 and the cam surface 510 of the disk cam 50.

Figure 6F:
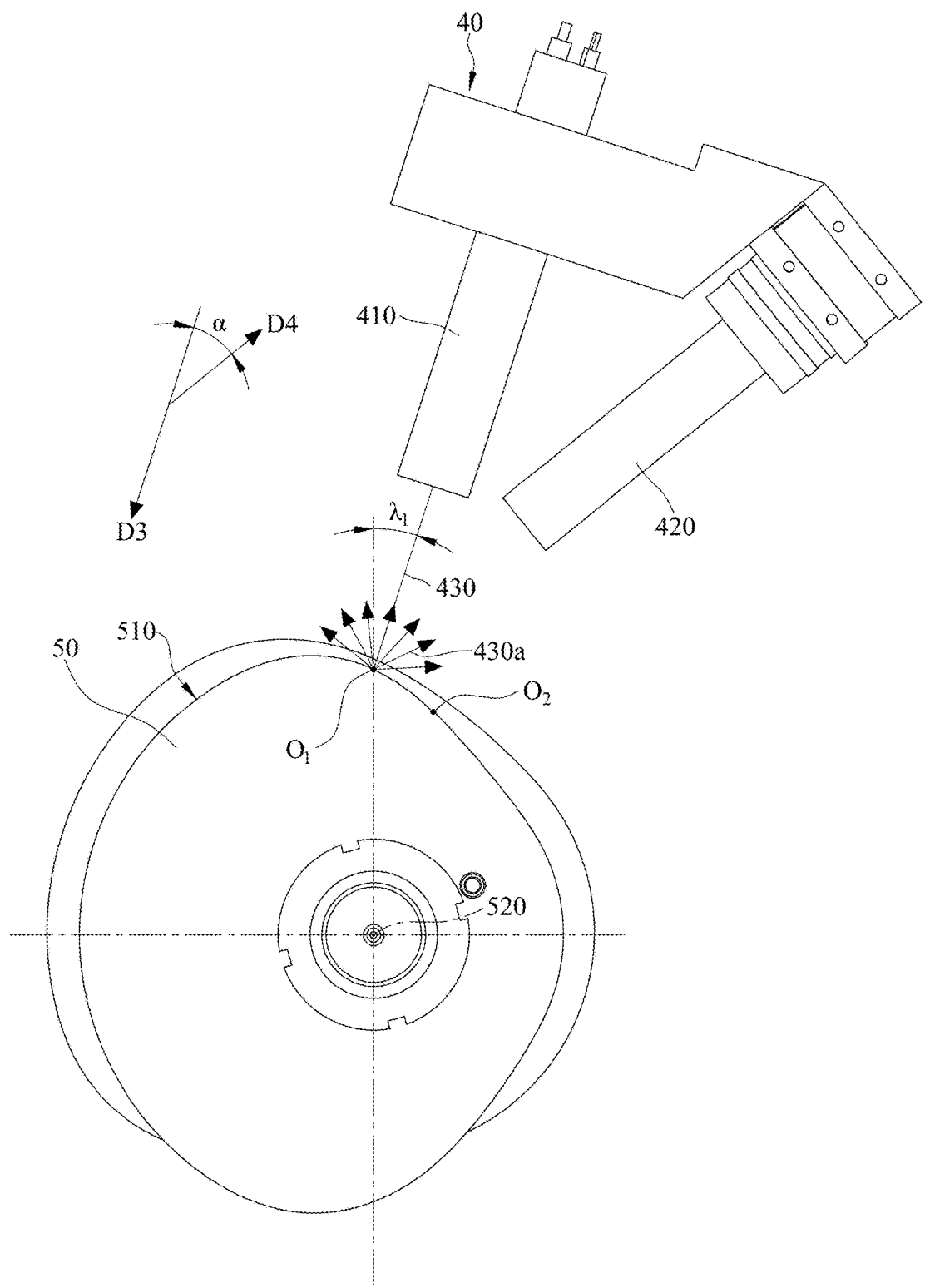

As shown in FIG. 6E and FIG. 6F, the step S44 is then executed. The computer 2 instructs the rotary motion stage 330 of the moving stage module 30 rotating a shift angle $\lambda_1$, and the shift angle $\lambda_1$ is between the radial and normal directions corresponding to the first profile point $O_1$ of the disk cam 50. When the step S44 is finished, the emitting direction D3 of the light beam 430 is parallel to the normal direction of the cam surface 510 of the disk cam 50 at the first profile point $O_1$.

In the non-contact and optical measuring method of this embodiment, the positioning procedure is executed in order from the step S41 to the step S44, but the present disclosure is not limited to this execution sequence. In some cases, the step 44 is executed before the step S43.

After the positioning procedure is finished, the step S5 is executed. The optical measuring module 40 is instructed by the computer 2 to execute a measuring procedure, so as to obtain a first grayscale measuring image corresponding to the first profile point $O_1$ and a second grayscale measuring image corresponding to second profile point $O_2$. As shown in FIG. 5D, in this embodiment, the step S5 includes steps S51 to S55.

As shown in FIG. 6F, the step S51 is executed first. The computer 2 instructs the optical measuring module 40 to perform a measurement for the first profile point $O_1$. In detail, the laser-emitting unit 410 of the optical measuring module 40 emits the light beam 430, and the light beam 430 is projected onto the first profile point $O_1$ of the disk cam 50 along the emitting direction D3. The light beam 430 projected onto the first profile point $O_1$ is reflected by the cam surface 510 of the disk cam 50 so as to generate a plurality of scattering light rays 430a. Some scattering light rays 430a travel along the receiving direction D4 to be received by the image-capturing unit 420 of the optical measuring module 40. The image-capturing unit 420 receives the scattering light rays 430a to capture the first grayscale measuring image corresponding to the first profile point $O_1$, and the first grayscale measuring image includes a profile speckle pattern resulting from laser speckles formed by the scattering light rays 430a.

Figure 6G:
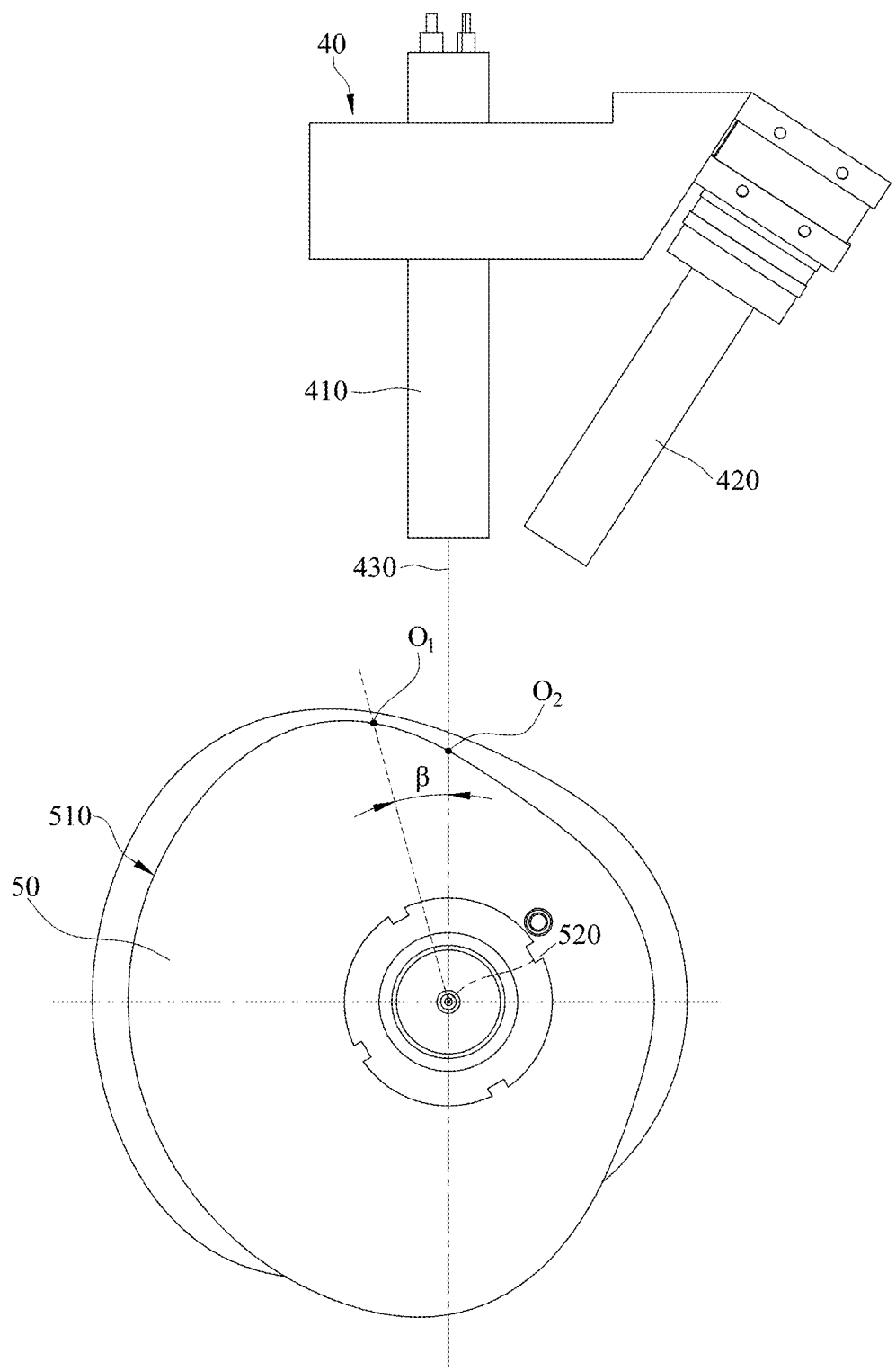

As shown in FIG. 6G, after the first grayscale measuring image corresponding to the first profile point $O_1$ is captured by the image-capturing unit 420, the step S52 is executed. The computer 2 instructs the rotating chuck 20 carrying the disk cam 50 to rotate a measuring angle β, thereby targeting the laser-emitting unit 410 of the optical measuring module 40 at the second profile point $O_2$. In this embodiment, the measuring angle β is about 30 degrees, but the value of the measuring angle β is not limited thereto.

Afterwards, the step S53 is executed. The computer 2 determines whether an accumulated measuring angle (the total angle which the disk cam 50 has rotated during the measuring procedure) is less than 360 degrees or not, thereby obtaining a determination result. If the determination result is negative, the computer 2 does not instruct the optical measuring module 40 measuring the second profile point $O_2$, and the measuring procedure is ended; if the determination result is positive, the measuring procedure is continued, and the computer 2 instructs the optical measuring module 40 performing a measurement for the second profile point $O_2$. In this embodiment, when the laser-emitting unit 410 of the optical measuring module 40 targets at the second profile point $O_2$, the accumulated measuring angle is about 30 degrees (that is, the accumulated measuring angle is 1×β, i.e. one times of the measuring angle β), so that the determination result is positive. The optical measuring module 40 continues the measuring procedure.

Regarding the measurement for the second profile point $O_2$, the step S54 is executed. The computer 2 instructs the rotary motion stage 330 of the moving stage module 30 rotating, so that the optical measuring module 40 is reset to an original state, and this original state, such as the height or the tilt of the optical measuring module 40, is existed before the step S44 is executed. When the step S54 is finished, the emitting direction D3, which is parallel to the normal direction of the cam surface 510 of the disk cam 50 at the first profile point $O_1$ in FIG. 6F, changes to pass through the rotational axis 520 of the disk cam 50 and be parallel to the second direction D2.

Figure 6H:
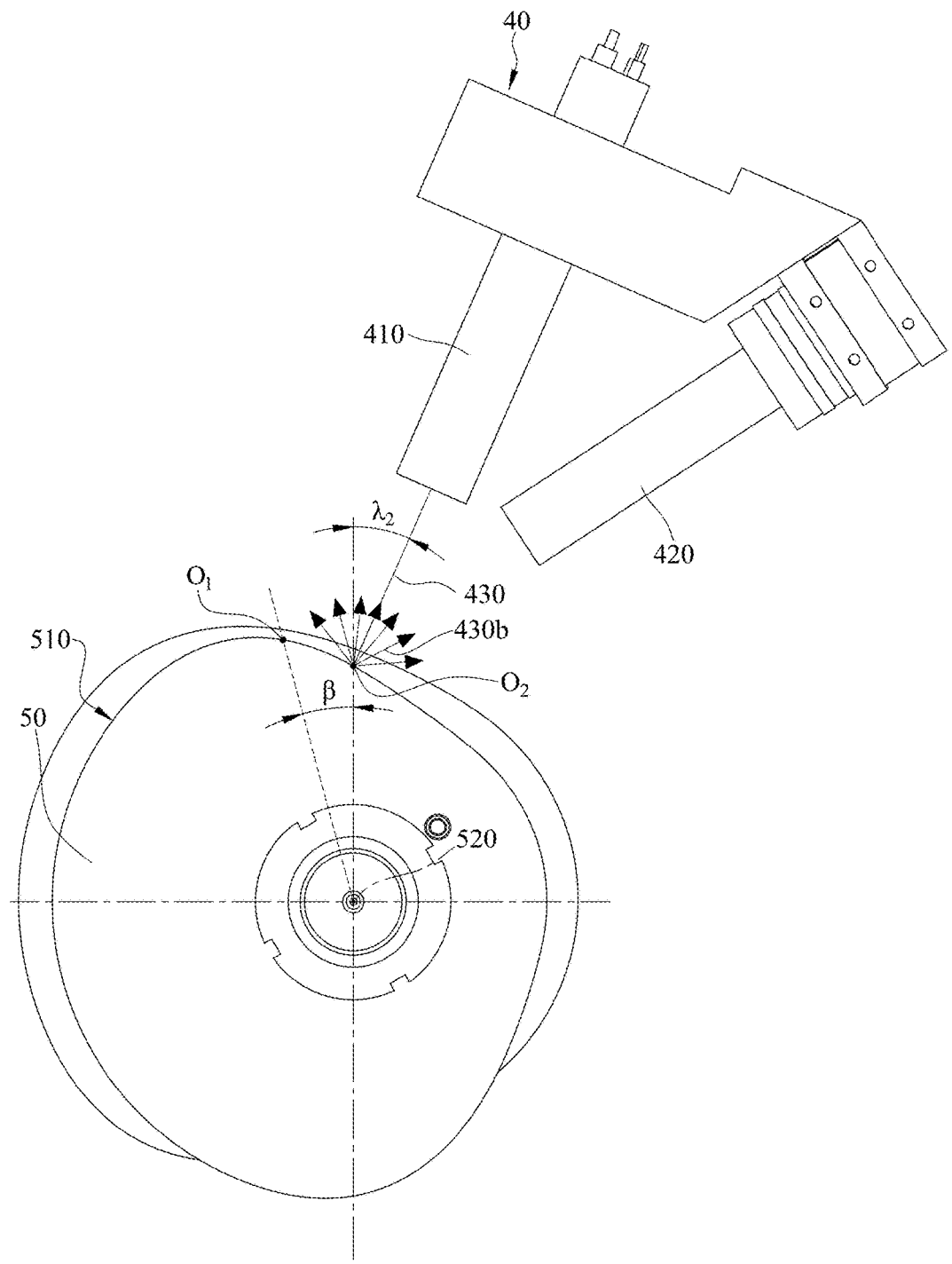

As shown in FIG. 6H, the step S55 is then executed. The computer 2 instructs the rotary motion stage 330 of the moving stage module 30 rotating a shift angle $\lambda_2$, and the shift angle $\lambda_2$ is between the radial and normal directions corresponding to the second profile point $O_2$ of the disk cam 50. When the step S55 is finished, the emitting direction D3 of the light beam 430 is parallel to the normal direction of the cam surface 510 of the disk cam 50 at the second profile point $O_2$.

The step S56 is then executed. The computer 2 instructs the optical measuring module 40 performing the measurement for the second profile point $O_2$. In detail, the light beam 430 emitted from the laser-emitting unit 410 of the optical measuring module 40 is projected onto the second profile point $O_2$ of the disk cam 50 in the emitting direction D3. The light beam 430 projected onto the second profile point $O_2$ is reflected by the cam surface 510 of the disk cam 50 so as to generate a plurality of scattering light rays 430b. Some scattering light rays 430b travel along the receiving direction D4 to be received by the image-capturing unit 420 of the optical measuring module 40. The image-capturing unit 420 receives the scattering light rays 430b to capture the second grayscale measuring image corresponding to the second profile point $O_2$, and the second grayscale measuring image includes a profile speckle pattern resulting from laser speckles formed by the scattering light rays 430b.

In the non-contact and optical measuring method of this embodiment, the measuring procedure is executed in order from the step S51 to the step S56, but the present disclosure is not limited to this execution order of steps S52 and S54. In other words, resetting the optical measuring module 40 (step S54) can be executed before the rotation of the disk cam 50 (step S52) in some cases.

After the second grayscale measuring image corresponding to the second profile point $O_2$ is captured by the image-capturing unit 420, the computer 2 instructs the rotating chuck 20 carrying the disk cam 50 to further rotate another measuring angle β, thereby targeting the laser-emitting unit 410 of the optical measuring module 40 at the next profile point (not shown in the drawings). The step S53 is then executed again to determine whether the accumulated measuring angle is less than 360 degrees or not. When the laser-emitting unit 410 of the optical measuring module 40 targets at said next profile point, the accumulated measuring angle is about 60 degrees (that is, the accumulated measuring angle is 2×β, i.e. two times of the measuring angle β), so that the determination result is still positive. The optical measuring module 40 continues the measuring procedure.

When all profile points on the cam surface 510 of the disk cam 50 are measured, the determination result in the step S53 is negative so that the measuring procedure is ended, and then the step S6 is executed. The computer 2 executes a value obtaining procedure to process the first grayscale measuring image and the second grayscale measuring image, and thus a profile speckle characteristic value of the profile speckle pattern in either the first grayscale measuring image or the second grayscale measuring image is obtained. As shown in FIG. 5E, in this embodiment, the step S6 includes steps S61 to S63.

The step S61 is executed firstly. The computer 2 calculates an averaged grayscale pixel value of the first grayscale measuring image and an averaged grayscale pixel value of the second grayscale measuring image. The calculation of the averaged grayscale pixel value can be referred to the details mentioned in the step S14 as well as equation (1) and will not be repeated hereafter.

The step S62 is then executed. The computer 2 performs a thresholding approach for the first grayscale measuring image, with the averaged grayscale pixel value of the first grayscale measuring image in the step S61 as a threshold value, to obtain a first binary measuring image. Also, the computer 2 performs the thresholding approach for the second grayscale measuring image, with the averaged grayscale pixel value of the second grayscale measuring image in the step S61 as the threshold value, to obtain a second binary measuring image. The steps of the thresholding approach can be referred to the details mentioned in the step S14 and will not be repeated hereafter.

The step S63 is then executed. A profile speckle pixel area of the profile speckle pattern in the first binary measuring image is calculated to obtain the profile speckle characteristic value corresponding to the first profile point $O_1$. Also, a profile speckle pixel area of the profile speckle pattern in the second binary measuring image is calculated to obtain the profile speckle characteristic value corresponding to the second profile point $O_2$. The calculation of the profile speckle pixel area can be referred to the details mentioned in the step S15, equations (2) and (3), and this calculation thereof will not be repeated hereafter. In this embodiment, the profile speckle pixel area is defined as the area in the binary measuring image occupied by the profile speckle pattern ($pixel^2$). The profile speckle pixel area in the first binary measuring image or the second binary measuring image is multiplied by a scale conversion value ($\mu m^2/pixel^2$) to obtain a profile speckle physical area ($\mu m^2$), and the profile speckle physical area is the aforementioned profile speckle characteristic value.

The profile speckle characteristic value in this embodiment is obtained by multiplying the profile speckle pixel area by the scale conversion value, but the disclosure is not limited thereto. In some cases, the profile speckle characteristic value of the profile speckle pattern is a ratio of the profile speckle pixel area to a total pixel area of the binary measuring image.

After the value obtaining procedure is finished, the step S7 is executed. The computer 2 executes a calculating procedure to substitute the profile speckle characteristic values into the roughness equation to obtain the surface roughness value of the cam surface 510 of the disk cam 50 at both the first profile point $O_1$ and the second profile point $O_2$. In detail, the profile speckle characteristic value of the profile speckle pattern in the first binary measuring image is substituted into the parameter 6 in the roughness equation [that is, equation (4)] by the computer 2 to obtain the arithmetical mean roughness value (Ra) of the cam surface 510 at the first profile point $O_1$; In addition, the profile speckle characteristic value of the profile speckle pattern in the second binary measuring image is also substituted into the parameter σ in the roughness equation by the computer 2 to obtain the arithmetical mean roughness value (Ra) of the cam surface 510 at the second profile point $O_2$.

After the calculating procedure is finished, the step S8 is executed. The arithmetical mean roughness values obtained in the step S7 are output and displayed on the human-machine interface 22 of the computer 2 for further data statistic and analysis.

Generally, the distribution of the scattering light generated by the reflection of the light beam 430 on the cam surface 510 of the disk cam 50 is close to a Gaussian distribution. In this embodiment, light emitted from the laser-emitting unit 410 of the optical measuring module 40 travels along the emitting direction D3, the image-capturing unit 420 is able to receive the scattering light traveling along the receiving direction D4, and the constant acute angle α subtended between the emitting direction D3 and the receiving direction D4 is ranged between 30.0 degrees and 60.0 degrees. Therefore, the constant acute angle α is favorable for the image-capturing unit 420 to receive more amount of scattering light and also favorable for the profile speckle pattern to be located at the center of the grayscale measuring image. When the profile speckle pattern is located closer to the center of the grayscale measuring image, the profile speckle characteristic value generated by the profile speckle pattern is more precise. Preferably, the constant acute angle α is 35.0 degrees. However, the present disclosure is not limited to the aforementioned value of the constant acute angle α.

Moreover, in this embodiment, the laser-emitting unit 410 emits the light beam 430 along the emitting direction D3 with the output power of the light beam 430 being less than or equal to 10 mW. Therefore, the scattering light, which is generated by the light beam 430 projected onto the cam surface 510, is prevented from having an excessive intensity so that it is favorable for reducing the damage on the image sensor of the image-capturing unit 420 due to the scattering light. Since the output power of the laser-emitting unit 410 is properly controlled, it is not necessary to install other optical members, such as reflective mirrors or filters, for the reduction of light intensity, thereby achieving compactness of the optical measuring module 40. The optical measuring module 40 with less optical members is prevented from interference and collision with the disk cam 50 or other members of the non-contact and optical measuring automation system 1.

Furthermore, in this embodiment, the second linear motion stage 320 of the moving stage module 30 is able to carry the optical measuring module 40 to move together, so as to adjust the distance between the optical measuring module 40 and the cam surface 510 of the disk cam 50. Therefore, when the optical measuring module 40 is overly close to the disk cam 50 so that a part of the disk cam 50 is located between the image-capturing unit 420 and the measured profile point, the second linear motion stage 320 is able to carry the optical measuring module 40 to simultaneously move away from the disk cam 50, thereby preventing the disk cam 50 from blocking a traveling path between the scattering light and the image-capturing unit 420. Also, it is favorable for focusing the image-capturing unit 420 on the disk cam 50 so as to ensure that the grayscale measuring image captured by the image-capturing unit 420 has high resolution.

According to the present disclosure, the laser-emitting unit of the optical measuring module emits the light beam, and the light beam is projected onto the cam surface of the disk cam. The light beam is reflected by the cam surface to generate local scattering light, and the image-capturing unit receives the local scattering light to capture a grayscale measuring image including the profile speckle pattern. The computer processes the grayscale measuring image to obtain the profile speckle characteristic value of the profile speckle pattern in the grayscale measuring image, and the computer calculates the surface roughness value of the cam surface according to the profile speckle characteristic value. Therefore, the usage of the non-contact and optical measuring method of the present disclosure is not restricted by the geometric form of cam profile, and the non-contact and optical measuring automation system does not contact the disk cam during the measurement of the surface roughness value, thereby solving the problems of low measuring efficiency and gradual wear of the stylus in the conventional contact type measuring equipment and method.

In addition, the computer instructs the rotary motion stage of the moving stage module carrying the optical measuring module to rotate together, so that the non-contact and optical measuring automation system is able to automatically adjust the emitting direction of the light beam emitted from the laser-emitting unit, thereby keeping the emitting direction parallel to the normal direction of the cam surface of the disk cam at the measured profile point. Therefore, it is favorable for simplifying the measuring procedure.

The foregoing description, for the purpose of explanation, has been described with reference to specific embodiments; however, the embodiments were chosen and described in order to best explain the principles of the disclosure and its practical applications, to thereby enable others skilled in the art to best utilize the disclosure and various embodiments with various modifications as are suited to the particular use contemplated. The embodiments depicted above and the appended drawings are exemplary and are not intended to be exhaustive or to limit the scope of the disclosure to the precise forms disclosed. Modifications and variations are possible in view of the above teachings.

What is claimed is:

1. A non-contact and optical measuring method, for measuring a surface roughness value of a cam surface of a disk cam, comprising steps of:
    setting a measuring parameter comprising at least one profile point on the cam surface and a normal direction of the cam surface at the at least one profile point;
    moving a laser emitter and a camera in a first direction by a first linear motion stage and in a second direction by a second linear motion stage to position the laser emitter and the camera under the disk cam, wherein the first direction is parallel to a rotational axis of the disk cam and second direction is orthogonal to the first direction, and rotating the disk cam around the rotational axis by a rotating chuck to target the laser emitter at the at least one profile point;
    executing a measuring procedure by the laser emitter and the camera, making a light beam emitted from the laser emitter project onto the at least one profile point, and making the camera receive a local scattering light, which is generated when the light beam is projected onto the at least one profile point, to capture at least one grayscale measuring image corresponding to the at least one profile point, wherein the at least one grayscale measuring image comprises a profile speckle pattern;
    executing a value-obtaining procedure by a computer, processing the at least one grayscale measuring image to obtain a profile speckle characteristic value of the profile speckle pattern in the at least one grayscale measuring image; and
    executing a calculating procedure by the computer, substituting the profile speckle characteristic value into a roughness equation to obtain the surface roughness value of the cam surface at the at least one profile point;
    wherein the step of executing the value-obtaining procedure comprises:
        calculating an averaged grayscale pixel value of the at least one grayscale measuring image;
        performing thresholding approach for the at least one grayscale measuring image, with the averaged grayscale pixel value as a threshold value, to obtain at least one binary measuring image;
        calculating a profile speckle pixel area of the profile speckle pattern in the at least one binary measuring image; and
        multiplying the profile speckle pixel area by a scale conversion value to obtain a profile speckle physical area, wherein the profile speckle physical area is the profile speckle characteristic value.

2. The non-contact and optical measuring method according to claim 1, further comprising a step of executing a positioning procedure, wherein the measuring parameter further comprises a cross-section to be measured located along an axial direction of the disk cam, the at least one profile point is located on the cross-section to be measured, and the step of executing the positioning procedure comprises:
    moving the laser emitter and the camera by the first linear motion stage and the second linear motion stage to align the laser emitter and the camera to the at least one profile point located on the cross-section to be measured; and
    rotating the laser emitter and the camera around the rotational axis of the disk cam by a rotary motion stage to make the light beam emitted from the laser emitter be parallel to the normal direction of the cam surface at the profile point.

3. The non-contact and optical measuring method according to claim 1, wherein the at least one profile point comprises a first profile point and a second profile point different from each other, and step of executing the measuring procedure comprises:

projecting the light beam emitted from the laser emitter onto the first profile point, wherein the local scattering light, which is generated when the light beam is projected onto the first profile point, is received by the camera;

rotating the disk cam by the rotating chuck for a measuring angle to target the laser emitter at the second profile point;

determining whether an accumulated measuring angle is less than 360 degrees to obtain a determination result, and ending the measuring procedure if the determination result is negative, or continuously executing the measuring procedure if the determination result is positive; and projecting the light beam emitted from the laser emitter onto the second profile point if the determination result is positive, wherein the local scattering light, which is generated when the light beam is projected onto the second profile point, is received by the camera.

4. The non-contact and optical measuring method according to claim 1, further comprising a step of executing a regression analysis procedure comprising:

providing a plurality of samples which are made of the same material as the disk cam, wherein each of the plurality of samples has a known surface roughness value, and the known surface roughness values are different from each other;

projecting the light beam emitted from the laser emitter onto surfaces of the plurality of samples vertically;

receiving the local scattering light, which is generated when the light beam is projected onto the plurality of samples, by the laser emitter to obtain a plurality of grayscale regression analysis images respectively corresponding to the plurality of samples, wherein each of the plurality of grayscale regression analysis images comprises a sample speckle pattern;

calculating an averaged grayscale pixel value of each of the plurality of grayscale regression analysis images;

performing thresholding approach for each of the plurality of grayscale regression analysis images, with the averaged grayscale pixel value as a threshold value, to obtain a plurality of binary regression analysis images;

calculating a sample speckle pixel area of the sample speckle pattern in each of the plurality of binary regression analysis images; and multiplying the sample speckle pixel area of the sample speckle pattern in each of the plurality of binary regression analysis images by a scale conversion value to obtain a sample speckle physical area, wherein the sample speckle physical area is a sample speckle characteristic value of the sample speckle pattern; and performing regression analysis for the sample speckle characteristic values and the known surface roughness values of the plurality of samples to obtain the roughness equation.

* * * * *